US010022451B2

(12) United States Patent
Xie et al.

(10) Patent No.: US 10,022,451 B2
(45) Date of Patent: Jul. 17, 2018

(54) ENCAPSULATED AGENTS AND METHODS OF MAKING AND USING THEREOF

(71) Applicant: University of Georgia Research Foundation, Inc., Athens, GA (US)

(72) Inventors: Jin Xie, Athens, GA (US); Zipeng Zhen, Athens, GA (US); Wei Tang, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 263 days.

(21) Appl. No.: 14/709,090

(22) Filed: May 11, 2015

(65) Prior Publication Data
US 2015/0320885 A1    Nov. 12, 2015

Related U.S. Application Data

(60) Provisional application No. 61/991,080, filed on May 9, 2014.

(51) Int. Cl.
| | |
|---|---|
| *A61N 5/06* | (2006.01) |
| *A61K 47/48* | (2006.01) |
| *A61K 31/704* | (2006.01) |
| *A61K 9/127* | (2006.01) |
| *A61K 41/00* | (2006.01) |
| *A61K 33/06* | (2006.01) |
| *A61K 33/22* | (2006.01) |
| *A61K 33/26* | (2006.01) |
| *A61K 33/30* | (2006.01) |

(52) U.S. Cl.
CPC ...... *A61K 47/48246* (2013.01); *A61K 9/1271* (2013.01); *A61K 31/704* (2013.01); *A61K 33/06* (2013.01); *A61K 33/22* (2013.01); *A61K 33/26* (2013.01); *A61K 33/30* (2013.01); *A61K 41/0057* (2013.01); *A61N 5/062* (2013.01); *A61N 2005/0662* (2013.01)

(58) Field of Classification Search
None
See application file for complete search history.

(56) References Cited

PUBLICATIONS

Xing et al. ("Characterization and cellular uptake of platinum anticancer drugs encapsulated in apoferritin," Journal of Inorganic Biochemistry 103 (2009) 1039-1044).*
Allémann et al. ("PEG-coated Poly(lactic acid) Nanoparticles for the Delivery of Hexadecafluoro Zinc Phthalocyanine to EMT-6 Mouse Mammary Tumours," J. Pharm. Pharmacol. 1995,47: 382-387).*
Yan et al. ("Apoferritin protein cages: a novel drug nanocarrier for photodynamic therapy," Chem. Commun., 2008, 4579-4581).*
Uchida et al. ("Targeting of Cancer Cells with Ferrimagnetic Ferritin Cage Nanoparticles," J. Am. Chem. Soc. 2006, 128, 16626-16633).*
Sigma-Aldrich, catalog search and record for cisplatin, downloaded from www.sigmaaldrich.com on Aug. 16, 2018.*
Bjork and Fish ("Native and Subunit Molecular Weights of Apoferritin," Biochemistry, vol. 10, No. 15, 1971, 2844-2848).*
Agostinis, P., et al., "Photodynamic Therapy of Cancer: An Update", CA Cancer J Clin., 2011, 61: 250-281.
Ali, M. F.,"Topical Delivery and Photodynamic Evaluation of a Multivesicular Liposomal Rose Bengal.", Lasers Med Sci, 2011, 26: 267-275.
Allemann, E., et al., "Peg-Coated Poly(Lactic Acid) Nanoparticles for the Delivery of Hexadecafluoro Zinc Phthalocyanine to Emt-6 Mouse Mammary Tumours", J Pharm Pharmacol, 1995, 47: 382-387.
Baas, P., et al., "Effect of N-Acetylcysteine on Photofrin-Induced Skin Photosensitivity in Patients", Lasers Surg Med, 1995, 16: 359-367.
Bechet D., et al., "Nanoparticles as Vehicles for Delivery of Photodynamic Therapy Agents", Trends in Biotechnology, 2008, 26: 612-621.
Berg, K., et al., "Porphyrin-Related Photosensitizers for Cancer Imaging and Therapeutic Applications", J Microsc, 2005, 218: 133-147.
Bessler, N. M., , "Verteporfin Therapy in Age-Related Macular Degeneration (Vam): An Open-Label Multicenter Photodynamic Therapy Study of 4,435 Patients", Retina, 2004, 24: 512.
Boyle, R. W., et al., "Hexadecafluorinated Zinc Phthalocyanine: Photodynamic Properties against the Emt-6 Tumour in Mice and Pharmacokinetics Using Zn-65 as a Radiotracer.", Br J Cancer, 1996, 73: 49-53.
Chatterjee, D. K., et al., "Nanoparticles in Photodynamic Therapy: An Emerging Paradigm", Adv Drug Deliv Rev, 2008, 60: 1627-1637.
Chen, B., et al., "Tumor Vascular Permeabilization by Vascular-Targeting Photosensitization: Effects, Mechanism, and Therapeutic Implications", Clin. Cancer Res., 2006, 12: 917-923.
Choi, H. S., et al., "Synthesis and in Vivo Fate of Zwitterionic near-Infrared Fluorophores.", Angew Chem Int Ed Engl, 2011, 50: 6258-6263.
Conte, C., et al., "Biodegradable Core-Shell Nanoassemblies for the Delivery of Docetaxel and Zn(Ii)-Phthalocyanine Inspired by Combination Therapy for Cancer", J Control Release, 2013, 167: 40-52.
D'Cruz, A. K., et al., "mThpc-Mediated Photodynamic Therapy in Patients with Advanced, Incurable Head and Neck Cancer: A Multicenter Study of 128 Patients", Head Neck, 2004, 26: 232-40.
Debefve, E., et al., "Leukocyte—Endothelial Cell Interaction Is Necessary for Photodynamic Therapy Induced Vascular Permeabilization", Lasers Surg. Med. 2011, 2011, 43: 696-704.
Dhami, S., et al., "Comparison of the Photophysics of an Aggregating and Non-Aggregating Aluminium Phthalocyanine System Incorporated into Unilamellar Vesicles", J Photoch Photobio A, 1996, 100: 77-84.

(Continued)

*Primary Examiner* — Christina Bradley
(74) *Attorney, Agent, or Firm* — Meunier Carlin & Curfman LLC

(57) ABSTRACT

The subject matter disclosed herein relates to compositions that contain a protein cage and a therapeutic agent, such as a photosensitizer. The protein cage is a protein that binds metal ion. The composition can further contain a cell recognition moiety. The methods disclosed are for permeabilizing the endothelial lining of a cancerous tissue or for treating a cancerous tissue to cause therapeutic injury resulting in the reduction of at least one of the surface area, the depth, and the amount of the tissue affected by the cancerous condition, in a subject.

31 Claims, 17 Drawing Sheets

(56) References Cited

PUBLICATIONS

Dolmans, D. E, et al., "Photodynamic therapy for cancer", Nat. Rev. Cancer, 2003, 3:380-387.
Dougherty T.J., et al., "Photoradiation Therapy for the Treatment of Malignant Tumors", Cancer Res, 1978, 38:2628-2635.
Dougherty, T. J., et al., "Photodynamic Therapy", J. Natl. Cancer Inst., 1998, 90: 889-905.
Dysart, J. S., et al., "Characterization of Photofrin photobleaching for singlet oxygen dose estimation during photodynamic Therapy of MLL cells in vitro" Phys. Med. Biol., 2005, 50: 2597-2616.
Edwards, B. K., et al., "Annual Report to the Nation on the Status of Cancer, 1975-2002, Featuring Population-Based Trends in Cancer Treatment", J. Natl. Cancer Inst., 2005, 97: 1407-1427.
Fabris, C., et al., "Photosensitization with Zinc (Ii) Phthalocyanine as a Switch in the Decision between Apoptosis and Necrosis", Cancer Res, 2001, 61: 7495-7500.
Fingar, V. H., "Vascular Effects of Photodynamic Therapy" J. Clin. Laser Med. Surg., 1996, 14: 323-328.
Fingar, V. H., et al., "Role of Thromboxane and Prostacyclin Release on Photodynamic Therapy-induced Tumor Destruction1", Cancer Res., 1990, 50: 2599-603.
Fisher, A, et al., "Clinical and Preclinical Photodynamic Therapy", Lasers Surg. Med., 1995, 17: 2-31.
Garcia, A. M., et al., "Photophysical Behaviour and Photodynamic Activity of Zinc Phthalocyanines Associated to Liposomes", Photochem. Photobiol. Sci., 2011, 10: 507-514.
Geninatti Crich, S., et al., "Magnetic Resonance Visualization of Tumor Angiogenesis by Targeting Neural Cell Adhesion Molecules with the Highly Sensitive Gadolinium-Loaded Apoferritin Probe", Cancer Res, 2006, 66: 9196-9201.
Gross, S., et al., "Monitoring Photodynamic Therapy of Solid Tumors Online by Bold-Contrast Mri", Nat. Med., 2003, 9: 1327-1331.
Hashizume, H., et al., "Openings between Defective Endothelial Cells Explain Tumor Vessel Leakiness", Am. J. Pathol., 2000, 156: 1363-1380.
Heldin, C. H., et al., "High Interstitial Fluidpressure—An Obstacle in Cancer Therapy", Nat. Rev. Cancer, 2004, 4: 806-813.
Kanthou, C., et al., "The Tumor Vascular Targeting Agent Combretastatin A-4-Phosphate Induces Reorganization of the Actin Cytoskeleton and Early Membrane Blebbing in Human Endothelial Cells", Blood, 2002, 99: 2060-2069.
Konan Y.N., et al., "State of the Art in the Delivery of Photosensitizers for Photodynamic Therapy", J Photochem Photobiol B., 2002, 66:89-106.
Konan, Y. N., et al., "Preparation and Characterization of Sterile Sub-200 Nm Meso-Tetra(4-Hydroxylphenyl)Porphyrin-Loaded Nanoparticles for Photodynamic Therapy", Eur J Pharm Biopharm, 2003, 55: 115-124.
Kong, G., et al., "Hyperthermia Enables Tumor-specific Nanoparticle Delivery: Effect of Particle Size", Cancer Res., 2000, 60: 4440-4445.
Kosharskyy, B., et al., "A Mechanism-Based Combination Therapy Reduces Local Tumor Growth and Metastasis in an Orthotopic Model of Prostate Cancer", Cancer Res, 2006, 66: 10953-10958.
Kovtun, Y. V., et al., "Cell Killing by Antibody—Drug Conjugates", Cancer Lett., 2007, 255: 232-240.
Less, J. R., et al., "Rapid Communication: Geometric Resistance and Microvascular Network Architecture of Human Colorectal Carcinoma", Microcirculation-Lon, 1997, 4: 25-33.
Lin, X., et al., "Chimeric Ferritin Nanocages for Multiple Function Loading and Multimodal Imaging", Nano Lett., 2011, 11: 814-819.
Lovell, J. F., et al., "Activatable Photosensitizers for Imaging and Therapy", Chem Rev, 2010, 110: 2839-2857.
Maeda, H., et al., "The EPR effect for macromolecular drug delivery to solid tumors: Improvement of tumor uptake, lowering of systemic toxicity, and distinct tumor imaging in vivo", Adv. Drug Deliv. Rev., 2013, 65:71-79.
Maeda, H., "Vascular permeability in cancer and infection as related to macromolecular drug delivery, with emphasis on the EPR effect for tumor-selective drug targeting", P. Jpn. Acad. B-Phys., 2012, 88: 53-71.
Maham, A., et al., "Protein-Based Nanomedicine Platforms for Drug Delivery", Small, 2009, 5: 1706-1721.
Moore, C. M., et al., "Photodynamic Therapy for Prostate Cancer—a Review of Current Status and Future Promise", Nat Clin Pract Urol, 2009, 6: 18-30.
Moore-Scott, B. A., et al., "New Serum-Free In Vitro Culture Technique for Midgestation Mouse Embryos", Genesis, 2003, 35: 164-168.
Nishiyama, N., et al., "Design and Development of Dendrimer Photosensitizer-Incorporated Polymeric Micelles for Enhanced Photodynamic Therapy", Adv. Drug Deliv. Rev., 2009, 61: 327-338.
Oda, K., et al., "Preparation of a Water-Soluble Fluorinated Zinc Phthalocyanine and Its Effect for Photodynamic Therapy", J Photoch Photobio B, 2000, 59: 20-25.
Orenstein A., et al., "Comparative Study of Tissue Distribution and Photodynamic Therapy Selectivity of Chlorin E6, Photofrin Ii and Ala-Induced Protoporphyrin Ix in a Colon Carcinoma Model", Br J Cancer, 1996, 73:937-944.
Prabhakar, U., et al., "Challenges and Key Considerations of the Enhanced Permeability and Retention Effect for Nanomedicine Drug Delivery in Oncology", Cancer Res, 2013, 73: 2412-2417.
Renno R.Z., et al., "Selective Photodynamic Therapy by Targeted Verteporfin Delivery to Experimental Choroidal Neovascularization Mediated by a Homing Peptide to Vascular Endothelial Growth Factor Receptor-2", Arch Ophthalmol., 2004, 122:1002-1011.
Selman, S. H., et al., "Transperineal Photodynamic Ablation of the Canine Prostate", J Urol, 1996, 156: 258-260.
Sharman W.M, et al., "Targeted Photodynamic Therapy via Receptor Mediated Delivery Systems", Adv Drug Delivery Rev, 2004, 56:53-76.
Sliwkowski, M. X., et al., "Antibody Therapeutics in Cancer", Science, 2013, 341: 1192-1198.
Snyder, J. W., et al., "Photodynamic therapy: a means to enhanced drug delivery to tumors", Cancer Res., 2003, 63: 8126-8131.
Steinberg, E.D, et al., "Porphyrin-based Photosensitizers for Use in Photodynamic Therapy", Tetrahedron 1998, 1998, 54:4151-4202.
Takahashi, T., et al., "Functional Properties of Threefold and Fourfold Channels in Ferritin Deduced from Electrostatic Calculations", Biophys J, 2003, 84:2256-2263.
Tan, M., et al., "Integrin Targeted Mr Imaging", Theranostics, 2011, 1: 83-101.
Taurin, S., et al., "Anticancer nanomedicine and tumor vascular permeability; Where is the missing link?" J. Control. Release, 2012, 164: 265-75.
Theil, E.C., "Structure, Gene Regulation, and Cellular Function in Animals, Plants, and Microorganisms.", Annu Rev Biochem, 1987, 56: 289-315.
Todd, T. J., et al., "Ferritin nanocages: great potential as clinically translatable drug delivery vehicles?", Nanomedicine (Lond), 2013, 8: 1555-1557.
Trachtenberg, J., et al., "Vascular-Targeted Photodynamic Therapy (Padoporfin, Wst09) for Recurrent Prostate Cancer after Failure of External Beam Radiotherapy: A Study of Escalating Light Doses", BJU Int, 2008, 102: 556-562.
Van Nostrum, C. F, , "Polymeric Micelles to Deliver Photosensitizers for Photodynamic Therapy", Adv Drug Deliv Rev, 2004, 54: 9-16.
Wang A. Z., et al., "Nanoparticle Delivery of Cancer Drugs", Annu. Rev. Med., 2012, 63: 185-98.
Yan, F., et al., "Apoferritin Protein Cages: A Novel Drug Nanocarrier for Photodynamic Therapy", Chem Commun (Camb), 2008, 4579-4581.
Yang, Z., et al., "Encapsulation of Platinum Anticancer Drugs by Apoferritin", Chem Commun (Camb), 2007, 3453-3455.
Zhang, Y., et al., "Multimodality Imaging of Integrin Alpha(V)Beta(3) Expression", Theranostics, 2011, 1: 135-148.
Zhen, Z., et al., "Ferritin Nanocages to Encapsulate and Deliver Photosensitizers for Efficient Photodynamic Therapy against Cancer", ACS Nano, 2013, 7: 6988-6996.

(56) References Cited

OTHER PUBLICATIONS

Zhen, Z., et al., "Rgd-Modified Apoferritin Nanoparticles for Efficient Drug Delivery to Tumors", J. ACS Nano, 2013, 7: 4830-4837.

* cited by examiner

ENCAPSULATED AGENTS AND METHODS OF MAKING AND USING THEREOF

ACKNOWLEDGEMENTS

This invention was made with government support under Grants 5R00CA153772, R01HL093339 and RR005351/GM103390 awarded by National Institutes of Health. The government has certain rights in the invention.

FIELD

The disclosed subject matter relates generally to cancer therapy, more particularly to compositions and methods for treating cancer by photodynamic activation of photosensitizers in a tissue affected by a cancerous condition.

BACKGROUND

Photodynamic therapy (PDT) is an emerging treatment modality that has shown promise for many types of disease, including cancer. However, selective delivery of photosensitizers (PS) to tumors remains a problem. In the clinic, PS delivery is achieved through a passive approach, by controlling the time that interval between the PS injection and light irradiation (Lovell J. F., et al., *Chem Rev.* 2010; 110:2839-2857). This lack of a targeting mechanism causes poor tumor selectivity, leading to a tumor/normal tissue accumulation ratio that is typically less than 2 (Orenstein A., et al., *Br J Cancer.* 1996; 73:937-944). As a result, PDT is often associated with off-target damage to the normal organs (e.g., the skin) and surrounding tissues. Patients undergoing PDT are required to stay away from sunlight, or even room light to avoid phototoxicity, a side effect that can last for 1-2 months (Dougherty T. J., et al., *Cancer Res.* 1978; 38:2628-2635).

Efforts have been made to improve the tumor selectivity of PSs, for instance, by coupling them with a tumor-targeting ligand such as an antibody (Renno R. Z., et al., *Arch Ophthalmol.* 2004; 122:1002-1011; Sharman W. M., et al., *Adv Drug Delivery Rev.* 2004; 56:53-76). However, issues such as low loading capacity, reduced phototoxicity, and heterogeneous expression of antigens throughout the tumor mass were found, and clinical translation of these technologies has not been seen. Alternatively, a PS can be loaded, via hydrophobic-hydrophobic interactions, into polymer- or liposome-based nanoparticles (Konan Y. N., et al., *J Photochem Photobiol B.* 2002; 66:89-106; Bechet D., et al., *Trends Biotechnol.* 2008; 26:612-621). This approach, however, is usually associated with a relatively low loading rate (less than 10 wt %) and a large particle size (around or larger than 100 nm), both factors can be detrimental to the PS delivery (Bechet D., et al. and Chatterjee D. K., et al., *Adv Drug Delivery Rev.* 2008; 60:1627-1637). There is a need for photosensitizers that have high tumor selectivity. There is also a need for photosensitizer carriers that have a high loading capacity.

Photosensitizers, while not toxic individually, can be activated by light of a specific wavelength. This causes energy transfer to near-by oxygen molecules that produces cytotoxic $^1O_2$. A common target in conventional PDT is the tumor vasculature (Nishiyama, N., *Adv. Drug Deliv. Rev.* 2009; 61: 327-338). In the clinic, vasculature PDT is achieved by controlling the time interval between photosensitizer injection and illumination, the so called "drug-light interval." Lacking selectivity, this toxicity acts on both endothelial and luminal targets (e.g. red blood cells/platelets), causing massive destruction that include vessel collapse and thrombus formation (Dolmans, D. E., et al., *Nat. Rev. Cancer* 2003; 3: 380-387). There is a need for photosensitizers for selective delivery that can be managed to increase vessel permeability but not induce occlusion. Particles injected subsequently can benefit from the permeabilized endothelium for enhanced accumulation in tumors. For example, unlike conventional small-molecule chemotherapeutics, nanoparticle- or macromolecule-based drugs can selectively egress at leaky tumor vasculatures and remain in the tumor interstitium for an extended period of time. However, despite relative leakiness compared to normal vessels, the endothelial lining can remain a barrier to the delivery of nanoparticles to tumors. This hindrance varies among tumors of different origins, stages, and organs, and may affect the treatment efficacy significantly. Prior work in this respect has focused on chemical-based vascular mediators such as nitroglycerin, ACE inhibitor, and PGE1 agonist (Maeda, H., et al., *Adv. Drug Deliv. Rev.* 2013; 65: 71-79). With these, a 2~3 fold increase of EPR effect in tumors can be achieved. This approach, however, may potentially cause side effects to normal vasculatures and organs due to the systematic nature.

What are needed are compositions comprising a photosensitizer and that can target cancer cells. Methods for treating cancer and methods for increasing the permeability of the tumor vasculature system are also needed. Further, methods for improving the efficacy of anti-tumor drugs in a subject are needed. The compositions and methods disclosed herein address these and other needs.

SUMMARY

In accordance with the purposes of the disclosed subject matter, as embodied and broadly described herein, this disclosure, in one aspect, relates to compositions for causing photodynamic damage to target cells. The compositions comprise a protein cage and a therapeutic agent. The protein cage can be a protein that binds metal ion. An exemplary protein cage is an apoferritin nanocage. The therapeutic agent can comprise a metal ion. Exemplary therapeutic moieties include photosensitizers, small molecules, proteins, antibodies, aptamers, metals, and cells. The disclosed compositions can further contain a cell recognition moiety.

Also disclosed are methods for permeabilizing the endothelial lining of a cancerous tissue within a subject's body. The methods include administering the compositions disclosed herein to a subject, allowing the compositions to accumulate in the affected cell, and irradiating the cell at an effective fluence rate and time, thereby causing an increase in the Enhanced Permeabilization and Retention (EPR) effect without causing significant occlusion and/or vessel collapse to cancerous cells. The fluence rate can be from about 3 mW/cm$^2$ to about 50 mW/cm$^2$ and the time duration for irradiating the cell can be from about 5 minutes to about 60 minutes. One or more anticancer drug can be administered to the subject to further cause therapeutic injury to the cancerous tissue. The anticancer drug
 can be a nanoparticle or a macromolecule.

A method for treating a cancerous tissue within a subject's body, thereby causing therapeutic injury resulting in the reduction of at least one of the surface area, the depth, and the amount of the tissue affected by the cancerous condition, is also disclosed. In these methods, the fluence rate of the radiation can be from about 50 mW/cm$^2$ to about 300 mW/cm$^2$ and the time duration for irradiating the cell can be from about 5 minutes to about 30 minutes.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying drawings, which are incorporated in and constitute a part of this specification, illustrate several examples of the disclosed subject matter and together with the description, serve to explain certain principles of the disclosed subject matter.

FIG. 1A is a schematic illustration of the formation and working mechanism of P-RFRTs. FIG. 1B shows photographs of P-RFRTs and free $ZnF_{16}Pc$ in PBS under different conditions. FIGS. 1C and 1D are AFM images of RFRTs (1C) and P-RFRTs (1D).

FIG. 3A is a bar graph showing the generation of $^1O_2$ at different concentrations. This was investigated using a Singlet Oxygen Sensor Green (SOSG) reagent. The study was performed by following a protocol provided by the vendor. Fluorescence signals at 525 nm were recorded 1 min after irradiation by a 671 nm laser. No difference was found between P-RFRTs and $ZnFe_{16}Pc$ (dispersed in PBS containing 1% tween-20) at all the concentrations, demonstrating that $ZnF_{16}Pc$ is not quenched in the nanocarriers. FIG. 3B is a graph showing the generation of oxygen from P-RFRTs (8 μg/mL) on day 0 and day 7 (kept in the dark during the period). No significant drop in fluorescence activates was found, indicating that the ability to generate $^1O_2$ was not affected.

FIG. 4A is an AFM image of P-RFRTs after irradiation with a 671 nm laser. Clusters of debris were found across the scope. FIG. 4B is an expanded view of the area in the white box in FIG. 4A.

FIG. 5A shows the uptake of P-RFRTs (50 μg $ZnF_{16}Pc$/mL) by U87MG cells at different time points. The uptake can be efficiently inhibited if c(RGDyK) (30×) was coincubated. The P-RFRTs were labeled with ZW800 (ex/em=780/800 nm). Scale bars, 50 μm. FIG. 5B shows the results from cell viability studies with P-RFRTs on U87MG cells. Elevated cytotoxicity (red fluorescence) was found with increased incubation time in the presence of light irradiation (671 nm, 0.1 W/cm² for 200 s). Without irradiation, no significant cell death was found. Gray, ethidium homodimer-1 (ex/em=528/617 nm), which stains dead cells. Scale bars, 50 μm.

FIGS. 7A-7B show MTT assay results with P-RFRTs (with and without irradiation) and free $ZnF_{16}Pc$ on U87MG cells from 12 h (FIG. 7A) and 24 h (FIG. 7B).

FIG. 8A shows in vivo and ex vivo fluorescence imaging results. P-RFRTs were i.v. injected, and images were taken at 1, 4, and 24 h. In the control group, c(RGDyK) (30×) was injected to block the tumor homing. The organs were arranged in the following order: (1) tumor; (2) heart; (3) liver; (4) spleen; (5) skin; (6) lung; (7) kidneys; (8) intestine; (9) muscle; (10) brain. FIG. 8B shows immunofluorescence microscopic imaging results. Integrin β3 is upregulated on both tumor vasculature and tumor cells. The distribution of P-RFRTs (ZW800, ex/em=780/800 nm) was correlated with the positive integrin β3 staining (Cy5, ex/em=650/670 nm), indicating that the tumor homing was mostly mediated by RGD-integrin interactions. In the control group, where c(RGDyK) was preinjected, minimal ZW800 signals were found in tumors. Scale bars, 50 μm. FIG. 8C is a plot showing a tumor growth curve. The animals were divided into four groups. Group 1: P-RFRTs, with irradiation. Group 2: P-RFRTs, without irradiation. Group 3: $ZnF_{16}Pc$, with irradiation. Group 4: PBS, without irradiation. Significant tumor suppression was found in group 1 ($P<0.05$). On day 12, a TIR of 83.64±2.52% was found. FIG. 8D is a plot showing a weight growth curve. No significant weight drop was found with animals injected with P-RFRTs, with or without irradiation. FIG. 8E shows caspase 3 staining with tumor tissues. High level of apoptosis was found in tumors from group 1 but not in the other control groups. The red areas are caspase 3 (Cy5, ex/em=650/670 nm); and the blue areas are DAPI. Scale bars, 50 μm. FIG. 8F shows H&E staining with tumor tissues. Densely packed neoplastic cells were found in the controls. In the treatment group, markedly disturbed tumor architecture was observed. Scale bars, 10 μm.

FIG. 10A shows caspase 3 staining with the skin tissues from animals treated with P-RFRTs. No obvious apoptosis was found, either with or without light irradiation. Red, caspase 3 (Cy5, ex/em=650/670 nm); blue, DAPI. Scale bars, 50 μm. FIG. 10B shows H&E staining with normal tissues. No abnormalities were observed. Scale bar, 100 μm.

FIG. 12A is an in vivo imaging study. P-RFRTs were labeled with IRDye800 and were i.v. administered into bilateral 4T1 tumor models. Fluorescence imaging performed at 24 h showed selective accumulation of P-RFRTs in both tumors (circled by yellow dashed lines). FIG. 12B is an ex vivo imaging with tumors as well as normal tissues. The normal tissues were arranged in the following order: First row—heart, liver, spleen and skin; Second row—intestine, kidney, muscle and brain. FIG. 12C are images showing immunofluorescence staining with tumor samples. Tumor vessels were stained by anti-integrin β3 antibodies. Scale bars, 100 μm.

FIG. 14A shows PDT-induced EPR enhancement. The study was performed in bilateral 4T1 tumor models. FIG. 14B shows the EPR enhancement effect, investigated in 4T1 tumor models which bear one tumor each. Animals were divided into three groups (n=3), and were treated with P-RFRTs plus irradiation, PBS plus irradiation, and P-RFRTs only, respectively. For ex vivo imaging, the tissues were arranged in the following order: The first row, heart, liver, spleen and skin; the second row, kidney, intestine, muscle and brain. FIG. 14C shows immunofluorescence staining. 'p' and 'c' indicates the peripheral and central regions of a tumor, respectively. Scale bars, 100 µm. FIG. 14D shows a SEM study on tumor sections. Scale bars, 2.5 µm.

FIG. 18A is a histogram comparison of relatively increased tumor uptake under irradiation at different fluence rates. The data were derived from ROI analyses on the in vivo imaging results. * Indicates P<0.05. FIG. 18B is immunofluorescence staining results. Scale bars, 100 µm. FIG. 18C shows EPR enhancement effect in different tumors (n=3).

FIG. 19A shows in vivo and ex vivo imaging. The study was performed in PC-3 tumor models. Fluorescence imaging was performed at 30 min, 1 h, 3 h, and 24 h to demonstrate the uptake of the probes by tumors (circled by red dashed lines). For each group, the tissues were arranged in the following order: The first row, tumor, heart, liver, spleen and skin; the second row, lung, kidneys, intestine, muscle and brain. FIG. 19B are histology studies on tumor tissues. Green, CD31. Red, HSA. Scale bars, 100 µm.

FIG. 20A shows in vivo and ex vivo imaging. The study was performed in MDA-MB-435s tumor models. Fluorescence imaging was performed at 30 min, 1 h, 3 h, and 24 h to illustrate the uptake of the probes by tumors (circled by red dashed lines). For each group, the tissues were arranged in the following order: The first row, tumor, heart, liver, spleen and skin; the second row, lung, kidneys, intestine, muscle and brain. FIG. 20B shows histology studies on tumor tissues. Green, CD31. Red, HSA. Scale bars, 100 µm.

FIG. 21A shows in vivo and ex vivo imaging. The study was performed in U87MG tumor models. Fluorescence imaging was performed at 30 min, 1 h, 3 h, and 24 h to evaluate the uptake of the probes by tumors (circled by red dashed lines). For each group, the tissues were arranged in the following order: The first row, tumor, heart, liver, spleen and skin; the second row, lung, kidneys, intestine, muscle and brain. FIG. 21B shows histology studies on tumor tissues. Green, CD31. Red, HSA. Scale bars, 100 µm.

FIG. 23A illustrates the EPR enhancement effect with QDs. The study was performed in bilateral 4T1 tumor models. Green, CD31, marking blood vessels. Red, QDs. Scale bars, 100 µm. FIG. 23B shows EPR enhancement effect with IONPs. The study was performed in bilateral 4T1 tumor models. FIG. 23C shows prussian blue staining on tumor samples from FIG. 23B. Scale bars, 100 µm.

FIG. 24A shows the therapy results, performed in 4T1 tumor models (n=5). FIG. 24B shows photographs of dissected tumors from FIG. 24A. FIG. 24C shows a body weight growth curves. FIG. 24D shows TUNEL assays on tumor sections. Green, TUNEL. Blue, DAPI. Scale bars, 100 µm.

DETAILED DESCRIPTION

Figures 1A, 1B, 1C, 1D:
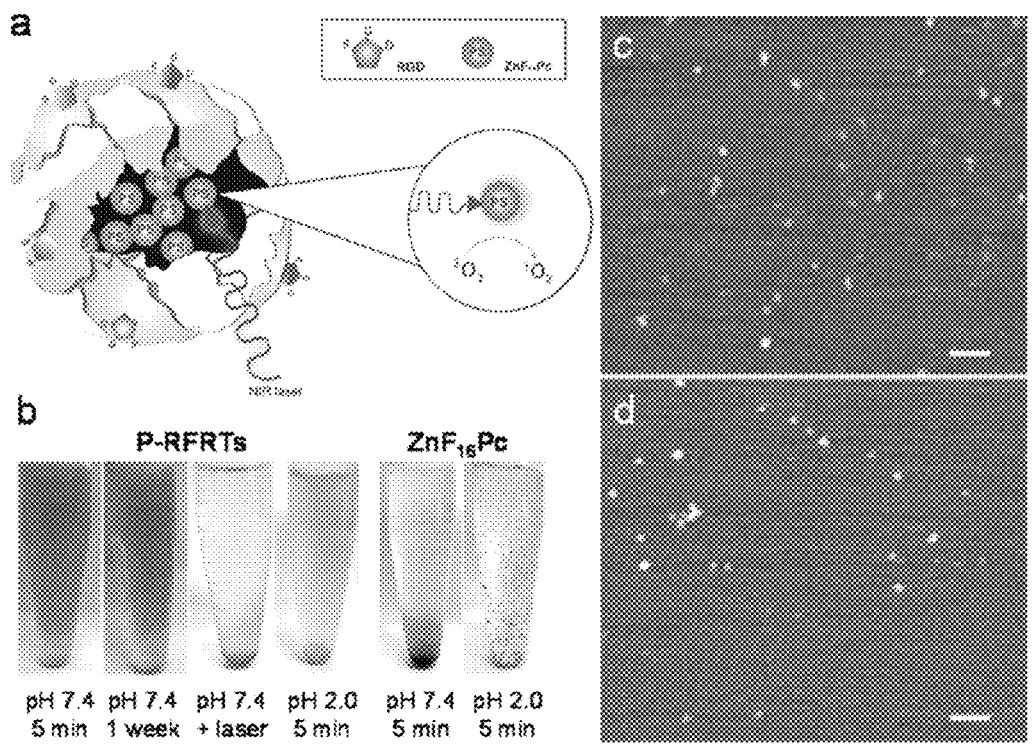
FIGS. 1A-1D show an illustration, photographs, and AFM images of P-RFRTs, $ZnF_{16}Pc$, and RFRTs.

The compounds, compositions, articles, devices, and methods described herein can be understood more readily by reference to the following detailed description of specific aspects of the disclosed subject matter and the Examples and Figures.

Before the present compounds, compositions, articles, devices, and methods are disclosed and described it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

In this specification and in the claims that follow, reference will be made to a number of terms, which shall be defined to have the following meanings:

As used in the description and the appended claims, the singular forms "a," "an," and "the" include plural referents unless the context clearly dictates otherwise. Thus, for example, reference to "a composition" includes mixtures of two or more such compositions, reference to "the photosensitizer" includes mixtures of two or more such photosensitizers, and the like.

"Optional" or "optionally" means that the subsequently described event or circumstance can or cannot occur, and that the description includes instances where the event or circumstance occurs and instances where it does not.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "apo", as used herein, is a prefix representing a protein having a cofactor or prosthetic group that is defective or removed.

As used herein, "ferritin" refers to a ferritin protein cage comprising mineralized iron in its cavity. "Apoferritin" refers to a ferritin protein nanocage with no iron loading in its cavity. Exemplary apoferritin nanocages include, but are not limited to nanocages comprising 24 subunits (e.g., a eukaryotic ferritin protein nanocage), or nanocages comprising 12 subunits (e.g., a bacterial "mini-ferritin" or Dps protein).

Compositions

The disclosed subject matter relates to compositions comprising a protein cage and a therapeutic agent. The protein cage can be a self-assembling protein cage. In some aspects, the protein cage can contain a metal binding site. The protein cage can be modified to impart functional capabilities for application in targeted therapeutic agent delivery. For example, the protein cage can be modified to include a therapeutic agent, an imaging agent, a recognition moiety, and combinations thereof. In some aspect, the modified protein cage is an apoprotein. For example, the compositions can contain an apoferritin nanocage, a therapeutic agent, and a target recognition moiety.

Protein Cage

The protein cage can be any protein that provides defined exterior and interior surfaces. Said another way, the protein cages contain a shell and a core area. Different protein cages lead to different sized cores. In some embodiments, protein cage cores can range from about 1 nm to about 30 nm (e.g. the internal diameter of the shells), from about 5 nm to about 24 nm (representing 8.5 to 28 nm outer shell diameters, in general, particularly when non-viral protein cages are used), from about 7 nm to about 20 nm, or from about 10 nm to about 15 nm. In other embodiments, a protein cage of about 12 nm (particularly where non-viral cages are utilized) or about 24 nm (particularly wherein viral cages are utilized) are suitable for use herein.

Suitable protein cages are those used for nucleic acid storage and transport, and iron mineralization and sequestration. Suitable protein cages that can be used in the compositions and methods disclosed include, but are not limited to, ferritin, heat shock proteins, lumazine synthase, Dps, or variants thereof. Specific examples of protein cages include, GroEL/GroES, the DnaK/DnaJ/GrpE, Hsp33, 60, 70, 90, 100. The ferritin nanocages include, but are not limited to, naturally-occurring ferritin, recombinant ferritin, synthetic ferritin, ferritin having a consensus amino acid sequence, and the like. Preferably, the compositions comprise apoferritin. Ferritin derived from both eukaryotes and prokaryotes can be used in the compositions. Specific examples include mammalian, bacterial, and equine spleen ferritin, particularly 12 and 24 subunit ferritins. Mammalian ferritin protein cages include two types of subunits: an H and an L subunit, and can accommodate about 4500 iron atoms within the cage. The outer diameter of mammalian ferritin is roughly 12 nm and the core is roughly 8 nm. Listeria innocua has a ferritin-like structure that catalyzes the oxidation of Fe(II) and is a dodecameric (12 subunits, rather than 24) protein.

Serum proteins and chaperones such as heat shock proteins that can load therapeutic agents through electrostatic forces or hydrophobic-hydrophobic interactions can also be employed. Suitable protein cages include 24 subunit heat shock proteins that form an internal core space. In particular, *Methanococcus jannaschii* assembles into a 24 subunit cage with 432 symmetry. Protein cages formed from the heat shock protein (Hsp) of *M. jannaschii* have a macromolecular structure of about a 12 nm exterior diameter and about a 6.5 nm interior diameter. These Hsp cages can be heated up to about 65° C. and are stable at a pH from about 6 to about 9. The superstructure of the Hsp cage includes 8.3 nm pores that render the interior cavity very accessible for interaction with various types of agents, as described herein.

Suitable protein cages also include proteins from the Dps (DNA-binding protein from starved cells) family. Dps proteins can be found in the Gram-positive bacterium Listeria innocua. Dps or Dps-like proteins can also be found in a variety of bacteria including, but not limited to, *E. coli*; *Helicobacter pylori*; *Halobacterium salinarum*; and *Bacillus anthracis*.

Other suitable protein cages include one or more *Sulfolobus solfataricus* protein subunits encoded by the ssdps gene. *S. solfataricus* proteins are known to be a Dps-like proteins. Such cages self-assemble into a hollow dodecameric protein cage having tetrahedral symmetry. The outer shell diameter is about 10 nm, and the interior diameter is ~5 nm. Dps proteins have been shown to protect nucleic acids by physically shielding DNA against oxidative damage and by consuming constituents involved in Fenton chemistry.

In some embodiments, the protein cage includes one or more *Pyrococcus furiosus* protein subunits encoded by the PfDps gene. *P. furiosus* proteins are known to be Dps-like proteins. Such cages self-assemble into a 12 subunit quaternary structure with an outer shell diameter of about 10 nm and an interior diameter of ~5 nm.

A variant of the protein cage can also be used. For example, the protein cage can have a replacement of an amino acid residue at a position affecting the chemical reaction field of a prosthetic group (e.g. a metal complex) received in the cavity of the protein with another amino acid residue. For example, a variant of ferritin can have a replacement of Glu 27 (site A) and Glu 107 (site B), the two axial ligands, by aspartate residues.

The protein cage has a cavity that has a high loading capacity/efficiency of the therapeutic agent. In some embodiments, the protein cage can be an apoprotein cage, that is a protein with its prosthetic group removed from the cavity. In some embodiments, the protein cage can contain from about 10 wt % to about 80 wt % of the therapeutic agent, e.g., a photosensitizer complex. The protein cage can contain from about 30 wt % to about 60 wt % of the therapeutic agent, from about 40 wt % to about 50 wt %, about 50 wt %, and at least about 30 wt %, at least about 40 wt %, at least about 50 wt %, at least about 60 wt %, at least about 65 wt % of the therapeutic agent. In this embodiment, the protein cage can contain at least about 1000 molecules of the therapeutic agent. In some embodiments the protein cage contains from about 1000 to about 1500, from about 1500 to about 2000, from about 2000 to about 2500, from about 2500 to about 3000, from about 3000 to about 3500 or from about 3500 to about 4500 molecules of the therapeutic agent In some embodiments, the protein cage is not sensitive to temperature, its surrounding physiological conditions, and/or to radiation. In some embodiments, the protein cage degrades when exposed to radiation in the range of from about 400 nm to about 900 nm, typically from about 600 nm to about 800 nm.

Therapeutic Agent

The compositions can also comprise a therapeutic agent. Therapeutic agent refers to a group that when administered to a subject, will cure or at least relieve to some extent, one or more symptoms of, a disease or disorder. Any suitable therapeutic agent can be used in the composition. Therapeutic agent include a wide variety of drugs, including antagonists, for example enzyme inhibitors, and agonists, for example a transcription factor which results in an increase in the expression of a desirable gene product (although as will be appreciated by those in the art, antagonistic transcription factors may also be used), are all included. In addition, therapeutic agent includes those agents capable of direct toxicity and/or capable of inducing toxicity towards healthy and/or unhealthy cells in the body. The therapeutic agent can be one that kills or inhibits cancer cells directly (e.g., cisplatin) or it can be one that can kill or inhibit a cancer cell indirectly (e.g., gold nanoparticles that kill or destroy cancer cells when heated using a light source).

Suitable therapeutic agents include, but are not limited to, photosensitizers, small molecules, metals, proteins, peptidomimetic compounds, aptamers, radionuclides, or any combination thereof. Other suitable therapeutic agents include, but are not limited to, a radioisotope linked to a protein as is the case with a radiolabeled protein, an antibody linked to an enzyme that metabolizes a substance, such as a prodrug, thus rendering it active in vivo, an antibody linked to a small molecule therapeutic agent, a radioisotope, a carbohydrate, a lipid, a thermal ablation agent, and a vaccine agent.

The therapeutic agent can be a nanoparticle. Suitable nanoparticles include, but are not limited to nanoparticle formulations of the anti-cancer agents, such as 13-cis-Retinoic Acid, 2-Amino-6-Mercaptopurine, 2-CdA, 2-Chlorodeoxyadenosine, 5-fluorouracil, 6-Thioguanine, 6-Mercaptopurine, Accutane, Actinomycin-D, Adriamycin, Adrucil, Agrylin, Ala-Cort, Aldesleukin, Alemtuzumab, Alitretinoin, Alkaban-AQ, Alkeran, All-transretinoic acid, Alpha interferon, Altretamine, Amethopterin, Amifostine, Aminoglutethimide, Anagrelide, Anandron, Anastrozole, Arabinosylcytosine, Aranesp, Aredia, Arimidex, Aromasin, Arsenic trioxide, Asparaginase, ATRA, Avastin, BCG, BCNU, Bevacizumab, Bexarotene, Bicalutamide, BiCNU, Blenoxane, Bleomycin, Bortezomib, Busulfan, Busulfex, C225, Calcium Leucovorin, Campath, Camptosar, Camptothecin-11, Capecitabine, Carac, Carboplatin, Carmustine, Carmustine wafer, Casodex, CCNU, CDDP, CeeNU, Cerubidine, cetuximab, Chlorambucil, Cisplatin, Citrovorum Factor, Cladribine, Cortisone, Cosmegen, CPT-11, Cyclophosphamide, Cytadren, Cytarabine, Cytarabine liposomal, Cytosar-U, Cytoxan, Dacarbazine, Dactinomycin, Darbepoetin alfa, Daunomycin, Daunorubicin, Daunorubicin hydrochloride, Daunorubicin liposomal, DaunoXome, Decadron, Delta-Cortef, Deltasone, Denileukin diftitox, DepoCyt, Dexamethasone, Dexamethasone acetate, Dexamethasone sodium phosphate, Dexasone, Dexrazoxane, DHAD, DIC, Diodex, Docetaxel, Doxil, Doxorubicin, Doxorubicin liposomal, Droxia, DTIC, DTIC-Dome, Duralone, Efudex, Eligard, Ellence, Eloxatin, Elspar, Emcyt, Epirubicin, Epoetin alfa, Erbitux, Erwinia L-asparaginase, Estramustine, Ethyol, Etopophos, Etoposide, Etoposide phosphate, Eulexin, Evista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR, Fulvestrant, G-CSF, Gefitinib, Gemcitabine, Gemtuzumab ozogamicin, Gemzar, Gleevec, Lupron, Lupron Depot, Matulane, Maxidex, Mechlorethamine, Mechlorethamine Hydrochlorine, Medralone, Medrol, Megace, Megestrol, Megestrol Acetate, Melphalan, Mercaptopurine, Mesna, Mesnex, Methotrexate, Methotrexate Sodium, Methylprednisolone, Mylocel, Letrozole, Neosar, Neulasta, Neumega, Neupogen, Nilandron, Nilutamide, Nitrogen Mustard, Novaldex, Novantrone, Octreotide, Octreotide acetate, Oncaspar, Oncovin, Ontak, Onxal, Oprevelkin, Orapred, Orasone, Oxaliplatin, Paclitaxel, Pamidronate, Panretin, Paraplatin, Pediapred, PEG Interferon, Pegaspargase, Pegfilgrastim, PEG-INTRON, PEG-L-asparaginase, Phenylalanine Mustard, Platinol, Platinol-AQ, Prednisolone, Prednisone, Prelone, Procarbazine, PROCRIT, Proleukin, Prolifeprospan 20 with Carmustine implant, Purinethol, Raloxifene, Rheumatrex, Rituxan, Rituximab, Roveron-A (interferon alfa-2a), Rubex, Rubidomycin hydrochloride, Sandostatin, Sandostatin LAR, Sargramostim, Solu-Cortef, Solu-Medrol, STI-571, Streptozocin, Tamoxifen, Targretin, Taxol, Taxotere, Temodar, Temozolomide, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Trastuzumab, Tretinoin, Trexall, Trisenox, TSPA, VCR, Velban, Velcade, VePesid, Vesanoid, Viadur, Vinblastine, Vinblastine Sulfate, Vincasar Pfs, Vincristine, Vinorelbine, Vinorelbine tartrate, VLB, VP-16, Vumon, Xeloda, Zanosar, Zevalin, Zinecard, Zoladex, Zoledronic acid, Zometa, Gliadel wafer, Glivec, GM-CSF, Goserelin, granulocyte colony stimulating factor, Halotestin, Herceptin, Hexadrol, Hexalen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, Idamycin, Idarubicin, Ifex, IFN-alpha, Ifosfamide, IL 2, IL-11, Imatinib mesylate, Imidazole Carboxamide, Interferon alfa, Interferon Alfa-2b (PEG conjugate), Interleukin 2, Interleukin-11, Intron A (interferon alfa-2b), Leucovorin, Leukeran, Leukine, Leuprolide, Leurocristine, Leustatin, Liposomal Ara-C, Liquid Pred, Lomustine, L-PAM, L-Sarcolysin, Meticorten, Mitomycin, Mitomycin-C, Mitoxantrone, M-Prednisol, MTC, MTX, Mustargen, Mustine, Mutamycin, Myleran, Iressa, Irinotecan, Isotretinoin, Kidrolase, Lanacort, L-asparaginase, and LCR. Exemplary nanoparticle compositions include, but are not limited to, Doxil, Abraxane, Depocyt, Myocet, MEPACT, Oncaspar, Genexol-PM, SMANCS, Feridex, GastroMARK, and combinations thereof.

The therapeutic agent can be a macromolecule. Suitable macromolecules include, but are not limited to, peptides, proteins such as hormones, enzymes, antibodies, antibody fragments, antibody conjugates, nucleic acids such as aptamers, iRNA, siRNA, microRNA, DNA, RNA, antisense nucleic acid or the like, antisense nucleic acid analogs or the like, or VEGF inhibitors. Exemplary macromolecular compositions include, but are not limited to, Cetuximab, Panitumumab, Trastuzumab, Pertuzumab, Ado-trastuzumab emtansine, Bevacizumab, Ipilimumab, Rituximab, Ofatumubab, Alemtuzumab. Brentuximab vedotin, Gemtuzumab ozogamicin, and combinations thereof.

The therapeutic agent can be a small molecule. For example, the small molecule can be an anti-cancer drug. Suitable small molecules include, but are not limited to, doxorubicin, Methotrexate, Paclitaxel, Cisplatin, carboplatin, Nedaplatin, oxaliplatin, heptaplatin, Iobaplatin, Bleomycin, docetaxel, gemcitabine, daunomycin, epirubicin, idarubicin, mitoxantrone, Valrubicin, Vorinostat, Gefitinib, Imatinib, Actinomycin, a ruthenium complex, and combinations thereof.

The therapeutic agent can contain a metal. In some embodiments, the metal can be a transition metal. Suitable metals include, but are not limited to, copper, zinc, cobalt, titanium, zirconium, vanadium, molybdenum, niobium, platinum, tin, aluminum, ruthenium, osmium, iron, rhenium, technetium, gold, gallium, gadolinium, manganese, nickel, silver, palladium, cadmium, indium, europium, or combinations thereof. In some embodiments, the therapeutic agent is doxorubicin linked to copper.

In some aspects, the therapeutic agent is a photosensitizer useful for causing photodynamic damage to cancer cells. Damage, as used herein, includes destruction of cellular organelles and subsequently suppression of cell growth, suppression of cell growth rate, and/or cell death. Therefore, photodynamic damage to cancer cells include, but is not limited to, preventing or reducing the development of a cancer, reducing the symptoms of cancer, suppressing or inhibiting the growth of an established cancer, preventing metastasis and/or invasion of an existing cancer, promoting or inducing regression of the cancer, inhibiting or suppressing the proliferation of cancerous cells, reducing angiogenesis or increasing the amount of apoptotic cancer cells, thereby treating cancer. These compositions contain a protein cage and a photosensitizer as the payload.

Any suitable photosensitizing agent can be used in the disclosed compositions and methods. The photosensitizer is a macrocyclic organic complex, which absorbs radiation in the range of from about 400 nm to about 900 nm, typically from about 600 nm to about 800 nm. The photosensitizers are capable of transferring their absorbed energy to molecular oxygen to generate singlet oxygen.

Examples of suitable macrocyclic organic complexes include, but are not limited to, porphyrin, pyrrole, tetrapyrrollic compound, expanded pyrrolic macrocycle and their derivatives, or combinations thereof. Specific examples of the macrocyclic compounds include, but are not limited to, green porphyrins, protoporphyrin, chlorins, tetrahydrochlorins (chlorins bacteriochlorins, isobacteriochlorins), hematoporphyrin, benzoporphyrin, texaohyrins, chlorophylls, dyes, aminolevulinic acid (ALA), silicon phthalocyanine Pc 4, m-tetrahydroxyphenylchlorine (mTHPC), mono-L-aspartyl chlorine (Npe6).pyropheophosphides, purpurins, texaphyrins, phenothiaziniums, phthalocyanines, napthalocyanines, porphycenes and pheophorbides.

The photosensitizers can contain metal cations. The metal ion present in the photosensitizer can be a diamagnetic metal. The metal ion present in the photosensitizer can be a diamagnetic metal. Suitable diamagnetic metals include, but are not limited to aluminum, copper, zinc, tin, silicon, germanium, lithium, magnesium, platinum, palladium, iridium, rhodium, ruthenium, rhenium, osmium, technetium, and combinations thereof. Suitable examples of metal-containing photosensitizers include, but are not limited to, zinc phthalocyanine, sulfonated aluminum phthalocyanine, and magnesium phthalocyanine, and zinc tetraphenyl porphyrin.

Target Recognition Moiety

The specificity of the compositions can be increased by conjugation of the composition with a target recognition moiety, which specifically binds to a component on the surface of, for example, a target cell or tissue. Target recognition moiety includes cell recognition moieties which specifically bind to receptors on the surface of a target cell. Steinberg, E. D., et al., (*Tetrahedron* 54:4151-4202 (1998)) discloses the design of new generations of photosensitizers for the treatment of tumors, the disclosure of which is incorporated herein by reference in its entirety for teachings of various cell recognition moieties. In the disclosed compositions, the cell recognition moiety can typically be present on the protein cage.

A wide variety of natural and synthetic molecules recognized by target cells can be used as the cell recognition moiety. Suitable cell recognition moieties include, but are not limited to, a receptor, ligand, polynucleotide, peptide, polynucleotide binding agent, antigen, antibody, or combinations thereof. In one embodiment, the cell recognition moiety is a peptide which has a length of from about 6 amino acids to about 25 amino acids. More specifically, the peptide amino acid sequence can be Cys-Asp-Cys-Arg-Gly-Asp-Cys-Phe-Cys (SEQ ID NO: 1), which interacts with integrin $\alpha_v\beta_3$. Integrin $\alpha_v\beta_3$ is overexpressed on tumor vasculatures and tumor cells.

The cell recognition moiety, for example the peptide amino acid sequence, can be similar, homologous, or a variant of cell recognition moieties in the art. In general, variants of the cell recognition moiety for example nucleic acids and peptides herein disclosed, can have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent similarity, or homology, to the stated sequence or the native sequence. Those of skill in the art readily understand how to determine the similarity of two polypeptides or nucleic acids. For example, the similarity can be calculated after aligning the two sequences so that the similarity is at its highest level.

Another way of calculating similarity, or homology, can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. Mol. Biol.* 48: 443 (1970), by the search for similarity method of Pearson and Lipman, *Proc. Natl. Acad. Sci.* U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.; the BLAST algorithm of Tatusova and Madden *FEMS Microbiol. Lett.* 174: 247-250 (1999) available from the National Center for Biotechnology Information, or by inspection.

The same types of similarity, or homology, can be obtained for nucleic acids by, for example, the algorithms disclosed in Zuker, M. *Science* 244:48-52, 1989, Jaeger et al. *Proc. Natl. Acad. Sci.* USA 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods may differ, but the skilled artisan understands if similarity is found with at least one of these methods, the sequences would be said to have the stated similarity.

As an example, peptides can have one or more conservative amino acid substitutions. These conservative substitutions are such that a naturally occurring amino acid is replaced by one having similar properties. Such conservative substitutions do not alter the function of the peptide.

The following references discloses antibodies, receptors, or receptor ligands that can be used to target specific proteins to tumor tissue: (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988);

Senter, et al., *Bioconjugate Chem.*, 4:3-9, (1993); Battelli, et al., *Cancer Immunol. Immunother.*, 35:421-425, (1992); Pietersz and McKenzie, Immunolog. Reviews, 129:57-80, (1992); and Roffler, et al., *Biochem. Pharmacol*, 42:2062-2065, (1991)), disclosure of which are incorporated herein by reference. The following references discloses vehicles such as "stealth" and other antibody conjugated particles (including lipid mediated drug targeting to colonic carcinoma), receptor mediated targeting through cell specific ligands, lymphocyte directed tumor targeting, and highly specific therapeutic retroviral targeting of murine glioma cells in vivo: (Hughes et al., *Cancer Research*, 49:6214-6220, (1989); and Litzinger and Huang, *Biochimica et Biophysica Acta*, 1104:179-187, (1992)), disclosure of which are incorporated herein by reference.

The protein cage complex can further contain a regulator. The regulator reduces or increases the rate of release of the photosensitizer from the protein cage. The regulator of the protein cage can be a peptide or a synthetic non-peptide moiety. Suitable peptides can have a length of from about 5 amino acids to about 50 amino acids, e.g., from about 5 amino acids to about 7 amino acids, from about 7 amino acids to about 10 amino acids, from about 10 amino acids to about 12 amino acids, from about 12 amino acids to about 15 amino acids, from about 15 amino acids to about 20 amino acids, from about 20 amino acids to about 25 amino acids, from about 25 amino acids to about 30 amino acids, from about 30 amino acids to about 40 amino acids, or from about 40 amino acids to about 50 amino acids.

Pharmaceutical Compositions

The compositions disclosed herein can be prepared as a pharmaceutical composition. For example, the compositions can further comprise a pharmaceutically acceptable excipient. The pharmaceutically-acceptable excipient can be administered with the photosensitizer compositions disclosed above. The pharmaceutical compositions can be administered in vivo in a pharmaceutically acceptable carrier. By "pharmaceutically acceptable" is meant a material selected to minimize any degradation of the active ingredient and to minimize any adverse side effects in the subject, as would be well known to one of skill in the art.

Suitable carriers and excipients are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

The compositions can be administered orally, parenterally (e.g., via intravenous injection, intraperitoneal injection, by intramuscular injection, intratumoral injection, intraarterial injection, transdermally, extracorporeally, topically or the like, including topical intranasal administration or administration by inhalant, or a combination thereof. As used herein, "topical intranasal administration" means delivery of the compositions into the nose and nasal passages through one or both of the nostrils and can comprise delivery by a spraying mechanism or droplet mechanism, or through aerosolization of the compositions. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be desirable.

Pharmaceutical compositions can further include one or more active ingredients such as antimicrobial agents, anti-inflammatory agents, anesthetics, and the like.

Methods of Use

Also described herein are methods of using the compositions disclosed herein. The compositions can be used to permeabilize the endothelium and/or vasculature system in tumors to improve the enhanced permeable and retention (EPR) effect in tumor cells. The compositions can also be used for treating a cancerous tissue within a subject's body.

Generally, the disclosed methods include contacting the tumor cell with an effective amount of the compositions as described herein. One of skill in the art recognizes that an amount can be considered therapeutically effective even if the condition is not totally eradicated but improved partially. The compositions can be injected directly into the target tissue, or can be administered systemically. More specifically, the compositions can be administered using any suitable method including intravenous (i.v.), intraperitoneal (i.p.), intramuscular (i.m.), intratumoral (i.t.), intraarterial (i.a.), topically, and/or inhalation. Intravenous administration is particularly preferred for solid tumors, while i.p. administration is preferred for pancreatic, liver, and gastric tumors. Advantageously, even when administered systemically, the compositions preferentially accumulate in the cancerous tissue, and preferably actively integrate in the cancerous tissue, as opposed to surrounding healthy tissue.

The composition can be administered before, during or after a tumor resection procedure. Examples of cancer types treatable by the compounds and compositions described herein include bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer. Further examples include cancer and/or tumors of the anus, bile duct, bone, bone marrow, bowel (including colon and rectum), eye, gall bladder, kidney, mouth, larynx, esophagus, stomach, testis, cervix, mesothelioma, neuroendocrine, penis, skin, spinal cord, thyroid, vagina, vulva, uterus, liver, muscle, blood cells (including lymphocytes and other immune system cells). Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma. Cancers that are preferably treated by the disclosed methods are lung, breast, brain, ovarian, lymphoma, leukemia, head and neck, pancreatic, and cervical, colon and rectum, endometrial, esophagus, liver, penile, skin-melanoma, skin-nonmelanoma, stomach, testicular, vaginal, uterine, vulvar, paranasal cancer, oropharyngeal, age-related macular degeneration, and laryngeal cancers.

Permeabilization of the Endothelium and/or Vasculature System

Also described herein are methods of using the compositions to permeabilize tumor tissues. Compositions containing a protein cage, a photosensitizer, and optionally a target recognition moiety can be used to permeabilize the endothelium and/or vasculature system in tumors to improve the enhanced permeable and retention (EPR) effect in tumor cells. Generally, the disclosed methods include contacting the tumor cell with an effective amount of the compositions as described herein. One of skill in the art recognizes that an amount can be considered therapeutically effective even if the condition is not totally eradicated but improved partially. For example, the amount of photosensitizer administered per each injection/dose will depend upon the subject, but can be about 0.5 to about 6 mg/kg body weight, about 1 mg/kg to about 5 mg/kg, about 1.5 mg/kg to about 4 mg/kg, about 1.5 mg/kg to about 3 mg/kg, for human therapies.

The compositions can be injected directly into the target tissue, or can be administered systemically. The photosensitizer composition is then allowed to accumulate in the endothelial cells of tumor tissues. This typically occurs within from about 0.1 hour to about 2 days, (e.g., about 0.1 hour, 0.2 hour, 0.3 hour, 0.4 hour, 0.5 hour, 0.6 hour, 0.7 hour, 0.8 hour, 0.9 hour, 1 hour, 1.5 hour, 2 hours, 2.5 hours, 3 hours, 4 hours, 5 hours, 6 hours, 7 hours, 8 hours, 9 hours, 10 hours, 11 hours, 12 hours, 15 hours, 18 hours, 20 hours, 22 hours, 24 hours, 27 hours, 30 hours) after administration, depending upon the subject. The photosensitizer composition is allowed to accumulate in the cancerous tissue for from about 30 minutes to about 120 hours post-administration of the composition. After the accumulation period, the cell is irradiated at an effective rate and time. An effective amount and time for irradiating the cancerous and/or tumor cells refer to a dose of radiation that produces an increase in cell damage or death or a dose of radiation that produces extravasation of the endothelial lining of tumor tissues. Numerous strategies for enhanced irradiation of tumors that are located within the human or mammalian body are discussed in the literature. Among these approaches is the use of high-energy lasers (instead of lamps), laser diodes, and bi- and multi-photon excitation of suitable chromophores.

The rate and time the cancerous cells are irradiated depends on the results required. For example, the cells can be irradiated at an effective fluence rate and time to cause permeabilization of the endothelial lining of the cancerous cells, i.e., increase in the Enhanced Permeabilization and Retention (EPR) effect without causing significant occlusion and/or collapse to tumor blood vessels.

The cancer and/or tumor cells are irradiated at a wavelength of from about 400 nm to about 900 nm. Typically, the wavelength is from about 550 nm to about 800 nm. The power/fluence rate for enhancing the EPR effect is from about 3 mW/cm$^2$ to about 50 mW/cm$^2$. Typically, the fluence rate is from about 5 mW/cm$^2$ to about 30 mW/cm$^2$. Preferably, the fluence rate is from about 8 mW/cm$^2$ to about 20 mW/cm$^2$. The cancerous/tumor cells are irradiating for any period from about 5 minutes to about 60 minutes, typically, from about 15 minutes to about 30 minutes.

After permeabilization, one or more additional agents (e.g. an anti-cancer nanoparticle- or macromolecule-based drugs that can selectively egress at leaky tumor vasculatures and remain in the tumor interstitium for an extended period of time, can be administered. The one or more additional agents are useful for therapeutic treatment. As used herein the term treating or treatment includes diminution, eradication, or delay in exacerbation of signs or symptoms after onset; and prevention of relapse.

In some embodiments, the one or more additional agents that can be administered after permeabilizing the tumor vasculature system are nanoparticles. Suitable nanoparticles are discussed herein. In some embodiments, the one or more additional agents that can be administered after permeabilizing the tumor vasculature system are macromolecules. Suitable macromolecules are discussed herein. The amount of agent administered per each injection/dose will depend upon the subject, and can be determined by one of skill in the art.

Treating a Cancerous Tissue

The cancerous cells can be irradiated at an effective fluence rate and time to cause therapeutic injury resulting in the reduction of at least one of the surface area, the depth, and the amount of the tissue affected by the cancerous condition. Typically, the cancer and/or tumor cells are irradiated at a wavelength of from about 400 nm to about 900 nm. Typically, the wavelength is from about 550 nm to about 900 nm. The power/fluence rate for enhancing the EPR effect is from about 50 mW/cm$^2$ to about 300 mW/cm$^2$. Typically, the fluence rate is from about 100 mW/cm$^2$ to about 300 mW/cm$^2$. Preferably, the fluence rate is about 300 mW/cm$^2$. The cancerous/tumor cells are irradiating for any period from about 5 minutes to about 60 minutes, typically, from about 15 minutes to about 30 minutes.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Ferritin Nanocages to Encapsulate and Deliver Photosensitizers for Efficient Photodynamic Therapy Against Cancer Surface-modified ferritin (FRT), a protein-based nanoparticle, was fabricated. In particular, Cys-Asp-Cys-Arg-Gly-Asp-Cys-Phe-Cys (SEQ ID NO: 1)-modified FRTs (RFRTs) (RGD4C-modified FRTs, RFRTs) were made. RFRTs were shown to encapsulate a large amount of zinc hexadecafluoro-phthalocyanine ($ZnF_{16}Pc$), a potent but rather hydrophobic photosensitizer (PS: $\lambda max=671$ nm; $\Phi\Delta=0.85$ in tetrahydrofuran17). RFRTs were also shown to selectively deliver the $ZnF_{16}Pc$ to tumors to induce PDT against cancer (FIG. 1).

The RFRTs were found to afford a high $ZnF_{16}Pc$ loading rate (as much as ~60 wt %) and a small post-loading size (less than 20 nm). In vivo studies with $ZnF_{16}Pc$-loaded RFRTs found a high tumor accumulation rate (tumor-to-normal tissue ratio of 26.82±4.07 at 24 h), a tumor inhibition rate (83.64% on day 12), as well as minimal toxicity to the skin and other normal tissues.

Preparation and Purification of RFRTs:

Production and purification of RFRTs have been reported previously. The DNA plasmid of RFRT was constructed by introducing the RGD4C peptide sequence to the N-terminus of Fn with restrictions sites, NcoI and XhoI, at the 5'- and 3'-ends, respectively. Primers were designed as follows: (+) 5' ATA TAC CAT GGG CTG CGA CTG CCG CGG AGA CTG CTT CTG CGG AGG CGG AGG CAC CAC CGC GTC T 3' (SEQ ID NO: 2); (—) 5' CCA GAC TCG AGT TAG CTC TCA TCA 3' (SEQ ID NO: 3). The double digested PCR product was ligated into NcoI/XhoI digested plasmid pRSF with T4 DNA ligase, and the ligation mixture was used to transform competent cells of E. coli XL1-Blue by standard procedures. The resulting pRSF/RFRT plasmids were screened by appropriate restriction digests, verified by DNA sequencing, and then used to transform the expression strain E. coli BL21(DE3). For expression, a 1 L LBkanamycin (50 µg/mL) culture of E. coli BL21(DE3)/RFRT was grown at 37° C. until an OD600 of 0.8 was reached. For induction, 1 mM IPTG was added to the culture and the culture was heated at 37° C. for 4 h. After sonication, the cell lysate was centrifuged at 10 400 rpm (12 930 g) for 30 min to remove the cell debris. The supernatant was heated at 60° C. for 10 min and centrifuged at 13 000 rpm for 30 min to remove the precipitates. 2-Mercaptoethanol (10 mM) was added to stabilize the product. The raw product was purified by HPLC using a Superose 6 size exclusion column. The concentration of RFRTs was determined by Bradford protein assay. The purified FRTs/RFRTs were stored at −80° C. For ZW800 labeling, RFRTs were incubated with ZW800-NHS for 30 min and purified through a NAP-5 column to remove uncoupled dye molecules. A starting ratio of 2:1 (ZW800-NHS to RFRTs) was used. The coupling efficiency was assessed spectroscopically by comparing with a predetermined standard curve (by monitoring absorbance at 780 nm). It was determined that the final conjugates have on average one ZW800 per particle.

Loading $ZnF_{16}Pc$ into FRTs/RFRTs:

The $ZnF_{16}Pc$ loading was achieved without breaking down the nanocages. Briefly, 10 µL of $ZnF_{16}Pc$ (5 mg/mL) in DMSO was dropwise added into 490 µL of RFRTs in PBS (0.5 mg/mL), and the mixture was gently shaken for ~45 min at room temperature. The raw products were then purified using a NAP-5 column to remove the unloaded $ZnF_{16}Pc$. The $ZnF_{16}Pc$ content was determined spectroscopically by comparing with a standard absorption curve of $ZnF_{16}Pc$. The protein concentration was determined by Bradford protein assay. The loading rate was expressed in weight percent (wt %).

In Vitro Assays:

U87MG cells were cultured in DMEM medium containing 10% nonessential amino acids, 10% fetal bovine serum, 0.1 mg/mL streptomycin sulfate, and 100 U/mL penicillin (MediaTech, USA) at 37° C. in a humidified atmosphere with 5% $CO_2$. For cell uptake studies, $10^5$ U87MG cells were seeded onto each well of a four-chamber slide (Labteck) one day prior to the studies. ZW800-labeled P-RFRTs were added to the solution to reach a final concentration of 50 µg $ZnF_{16}Pc$/mL. In the control group, 30× free c(RGDyK) was used to co-incubate with P-RFRTs. At different time points, incubation was stopped. The cells were washed with PBS five times and fixed with 75% ethanol overnight at 4° C. The slides were mounted with DAPI containing mounting medium (Vector Inc.) and imaged under an Olympus X71 fluorescence microscope. For PDT studies, the cells were exposed to a 671 nm laser at 0.1 W/cm$^2$ for 200 s. The cell viability was determined by MTT assays using a gradient of P-RFRTs ($ZnF_{16}Pc$ concentrations of 3, 6.25, 12.5, 25, and 50 µg/mL). In control groups, either no irradiation was applied or free $ZnF_{16}Pc$ at the same dose was used. Live/dead assays were performed by following a protocol provided by the vendor.

Animal Models:

Animal models were established by subcutaneous injection of $10^6$ human glioblastoma U87MG onto the hind legs of 5-6 week athymic nude mice (Harlan). Animal studies were performed according to a protocol approved by the Institutional Animal Care and Use Committee (IACUC) of University of Georgia.

In Vivo Imaging:

The imaging studies were performed when tumors reached a size between 350 and 500 mm$^3$. ZW800-labeled P-RFRTs (5 mg RFRT/mL) was intravenously (i.v.) injected into mice (n=3). For the control group, 30× c(RGDyK) was administrated 30 min prior to the RRFRT injection (n=3). Fluorescence images were acquired on a Maestro II imaging system using an orange filter (640 to 820 nm) at 1, 4, and 24 h time points. The images were unmixed using the Maestro software. The average signal ($10^6$ photons/cm$^2$/s) for each region of interest (ROI) was measured. Tumor-to-normal tissue ratio (T/N) was determined and was expressed as mean±SD. All mice were euthanized after the 24 h imaging. Tumors as well as major organs were collected and subjected to ex vivo imaging. After imaging, the tissues were snapfrozen in O.C.T. (Tissue-Tek) and stored in a −80° C. freezer.

Therapy Studies:

For PDT studies, 20 mice bearing U87MG tumors were randomly divided into four groups. The treatment scheme is as follows: (1) P-RFRTs (1.5 mg $ZnF_{16}Pc$/kg), with irradiation; (2) P-RFRTs (1.5 mg $ZnF_{16}Pc$/kg), without irradiation; (3) free $ZnF_{16}Pc$ (1.5 mg $ZnF_{16}Pc$/kg), with irradiation; (4) PBS, no irradiation. The photoirradiation was applied 24 h after the injection of P-RFRTs (671 nm laser, 0.3 W/cm$^2$ for 15 min). The tumor sizes and body weights were inspected every 3 days. The tumor weight was estimated using the formula, tumor volume=length×(width)$^2$/2, assuming a tumor density of 1 mg/mL. After therapy, major organs as well as tumors were collected and sectioned to 8 µm slices for caspase 3 and H&E staining.

Immunofluorescence Staining:

The cryogenic slides were fixed with cold acetone for 30 min, washed by running water for 5 min, and blocked by 10% goat serum for 1 h. Anti-integrin β3 or anti-caspase 3 antibodies were incubated with the slides at 4° C. overnight. Cy5.5-labeled secondary antibody was then added and incubated for 1 h at 37° C. After gently rinsing with PBS, the slides were mounted and ready for microscopic imaging.

H&E Staining:

H&E staining was performed according to a protocol provided by the vendor (BBC Biochemical). Briefly, 8 μm cryogenic slides were prepared and fixed with 10% formalin for about 30 min at room temperature. After washing with running water for 5 min, the slides were treated with gradient concentrations of alcohol (100, 95, and 70%), each for 20 s. The hematoxylin staining was performed for about 3 min and washed with water for 1 min. The eosin staining was performed for about 1 min. The slides were washed, treated with xylene, and mounted with Canada balsam. The images were acquired on a Nikon Eclipse 90i microscope.

The drug loading was achieved by adding $ZnF_{16}Pc$ in DMSO into a RFRT solution in 0.01 M PBS (pH 7.4) and, after that, incubating at room temperature for 45 min. The raw products were subjected to purification through a NAP-5 column to remove the unloaded $ZnF_{16}Pc$. The starting concentrations of $ZnF_{16}Pc$ and RFRT were tuned, and the loading capacity was investigated (Table 1).

TABLE 1

Drug loading efficiency of RFRT at different conditions

| $ZnF_{16}Pc$ to RFRT ratio (w/w) | Loading rate (wt %) | Yield (%)[a] |
|---|---|---|
| 1:20 | 19.7 | 75.6 |
| 1:10 | 35.7 | 53.0 |
| 1:5 | 41.3 | 37.5 |
| 1:2 | 60.0 | 33.6 |
| 1:2; pre-incubation with Cu(II)[b] | 25.1 | 41.4 |

$ZnF_{16}Pc$ (5 mg/mL) in DMSO was added dropwise to RFRTs in PBS (0.5 mg/mL). The final volume was 500 μL. The mixture was gently shaken for ~45 min at room temperature. The raw products were then purified using a NAP-5 column to remove the unloaded $ZnF_{16}Pc$. The $ZnF_{16}Pc$ content was determined spectroscopically by comparing with a standard absorption curve of $ZnF_{16}Pc$. The protein concentration was determined by Bradford protein assay.
[a]It is determined by comparing the amount of protein before and after the drug loading.
[b]Cu(II) was added first to an RFRT solution (8:1, w/w). The Cu-loaded RFRTs were then incubated with $ZnF_{16}Pc$.

Figure 2:
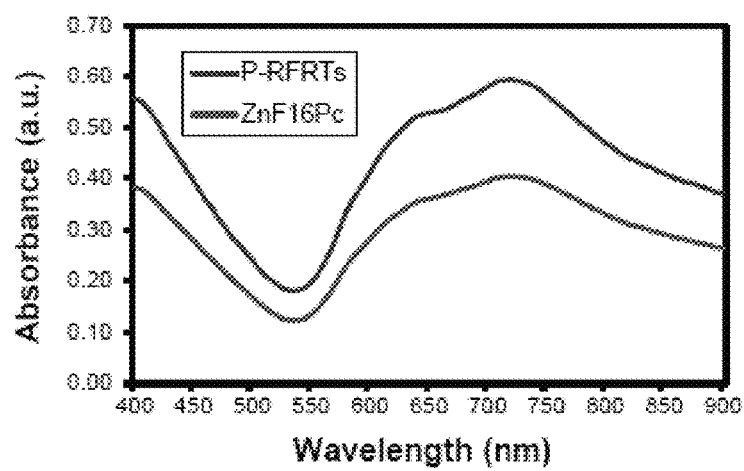
FIG. 2 is a plot of the absorbance spectra of P-RFRTs in PBS and $ZnF_{16}Pc$ in PBS containing 1% tween-20.

It was found that 1 mg of RFRTs can load up to 1.5 mg of $ZnF_{16}Pc$, yielding a loading rate as high as 60 wt %. For stability considerations, however, a formulation with a loading rate of 41.2 wt % was used for the current investigations. The absorption spectra of P-RFRTs and free $ZnF_{16}Pc$ are shown in FIG. 2. The sizes of the nanoparticles were determined by atomic force microscopy (AFM) analysis (FIGS. 1C and 1D). An overall comparable sizes before and after the $ZnF_{16}Pc$ loading (18.3±4.1 nm for RFRTs and 18.6±2.6 nm for P-RFRTs) was found.

Despite the heavy loading, the resulting P-RFRTs are highly stable in PBS. A photograph of P-RFRTs in PBS is shown in FIG. 1B. The solution was stable for more than a week without visible precipitation. In comparison, free $ZnF_{16}Pc$ at the same concentration quickly precipitated out due to its poor solubility. The stability of P-RFRTs at pH=2 was also investigated. Within 10 min, a large amount of blue precipitation had formed at the bottom of the vial (FIG. 1B). It is known that FRT nanocages are disassembled at pH 2.0. This pH-induced unloading demonstrated that the cargo was mostly internalized into hollow cores of the nanocages and was released upon particle decomposition.

Figures 3A, 3B:
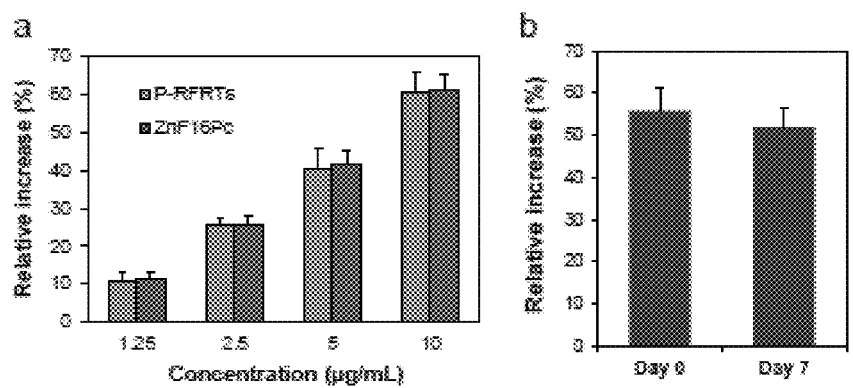
FIGS. 3A-3B are bar graphs of the showing the generation of singlet oxygen.
Figures 4A, 4B:
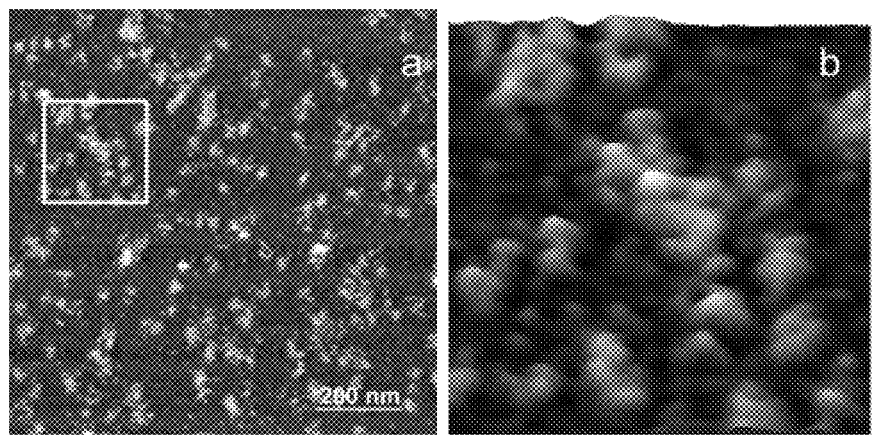
FIGS. 4A-4B are AFM images of P-RFRTs.

The generation of $^1O_2$ was studied using a singlet oxygen sensor green (SOSG) reagent (Invitrogen). SOSG is essentially a dye that is fluorescently quenched in its intact form but, upon activation in response to $^1O_2$, produces an increase of fluorescence signals at 525 nm. P-RFRTs at different concentrations with the SOSG reagent were incubated. The samples were then irradiated with a 671 nm laser. The relative increase of readings at 525 nm was recorded 1 min later. As a comparison, $ZnF_{16}Pc$ was dispersed in PBS containing 1% tween and subjected to the analyses at the same conditions (FIG. 3). No significant difference between the results from the two groups was found, demonstrating that $ZnF_{16}Pc$ is not quenched in the nanocarriers. The post-irradiated P-RFRTs under AFM was also examined. Instead of finding ~20 nm nanoparticles, clusters of debris across the scope was observed (FIG. 4). The particle destruction was attributed to the $^1O_2$ generated during the irradiation. This agrees with the above observation that $ZnF_{16}Pc$ was unloaded upon particle decomposition.

Figures 5A, 5B:
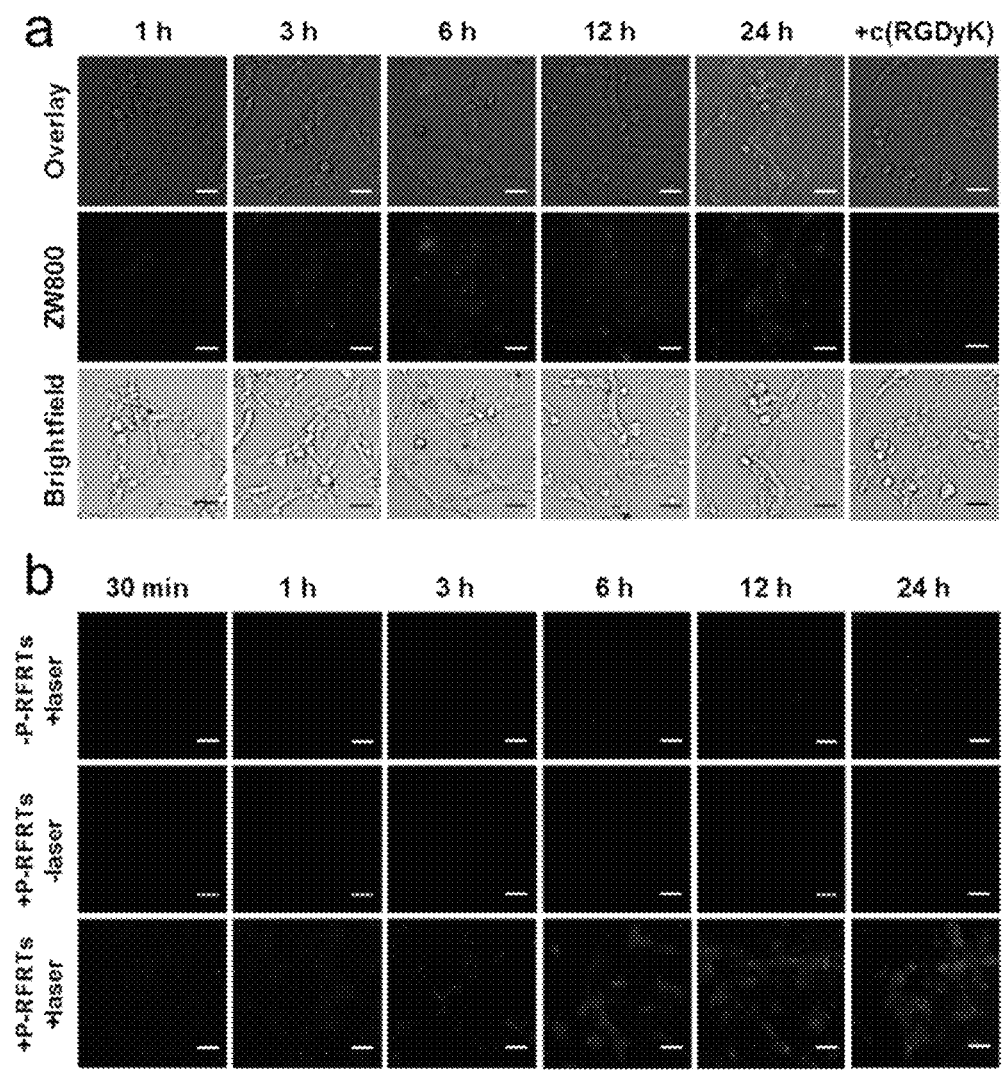
FIGS. 5A-5B are images, from cell viability studies, showing the uptake of P-RFRT.
Figure 6:
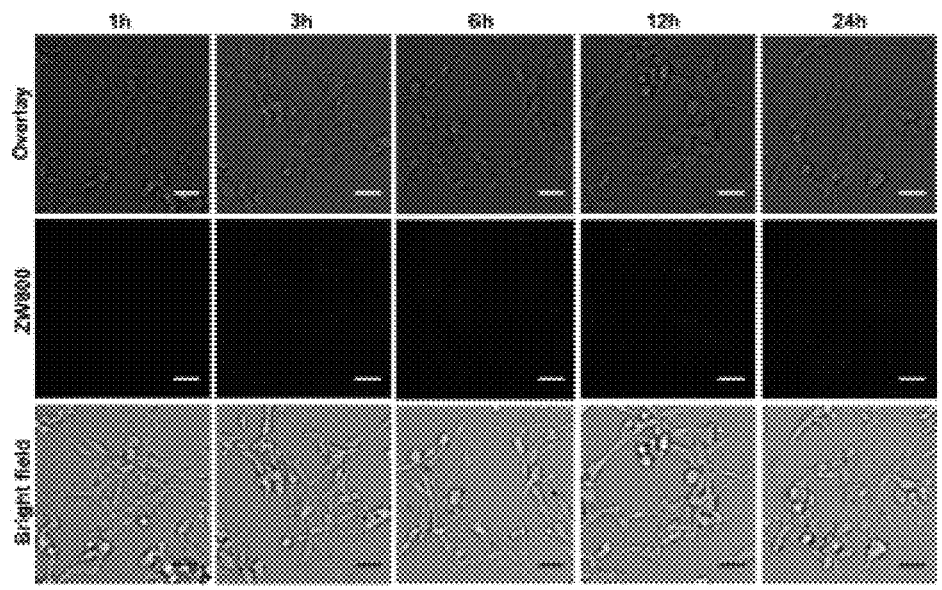
FIG. 6 is a group of images showing the internalization of ZW800-labeled RFRTs by U87MG cells in the presence of free c(RGDyK) (30×).

The drug loading effect on the particles' ability to interact with integrin αvβ3 was studied. To facilitate the tracking of particles, P-RFRTs were labeled with ZW800, a near-infrared dye molecule (ex/em=780/800 nm). The coupling ratio was controlled so that on average one ZW800 was coupled to one RFRT. The in vitro studies were performed with U87MG human glioblastoma cells, which are known to express a high level of integrin $α_vβ_3$. As shown in FIG. 5A, P-RFRTs demonstrated time-dependent internalization by U87MG cells. This internalization was blocked when free c(RGDyK) (30×, relative to protein concentration; it is noted that there are 24 RGD4C moieties on the surface of each RFRT nanoparticle) was coincubated (FIG. 5A and FIG. 6). The results demonstrate that, despite the heavy loading, P-RFRTs kept the targeting specificity toward integrin αvβ3.

Figures 7A, 7B:
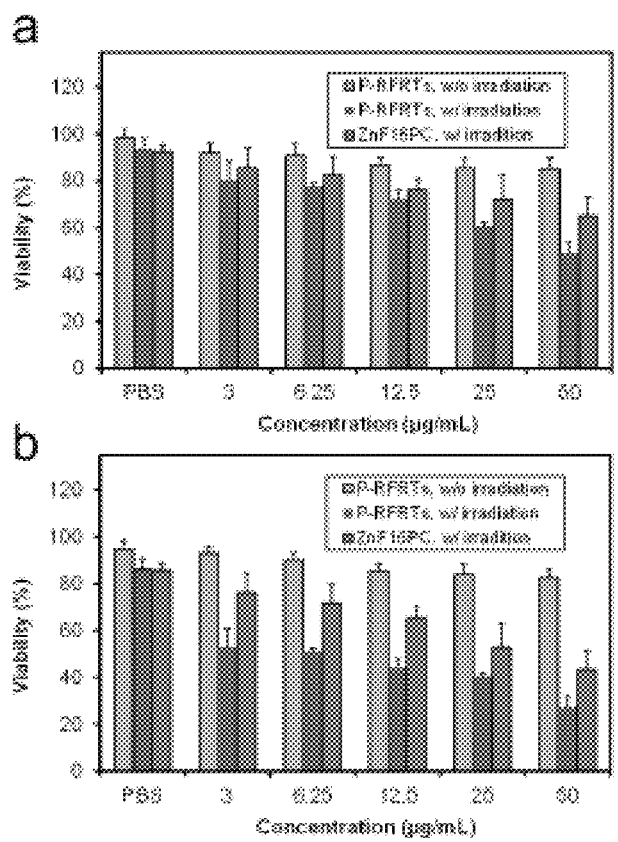
FIGS. 7A-7B are bar graphs showing results from MTT assay.

The particles' phototoxicity was also studied with U87MG cells. Briefly, cells were incubated with P-RFRTs in the dark and at different time points and then irradiated with a 671 nm laser (0.1 W/cm$^2$, 200 s). The cell viability was studied 120 min post-irradiation by ethidium homodimer-1 staining (Invitrogen), which marked dead cells (FIG. 5B). Increased red fluorescence was found to be correlated with elevated incubation time and was suppressed when free c(RGDyK) (30×) was coincubated. On the other hand, if no laser was applied, the red fluorescence remained at a background level. Similar observations were made from MTT assays, which showed a marginal drop in cell viability when there was no light irradiation and concentration-dependent cell death when there was (FIG. 7). These observations confirmed that cytotoxicity only occurs when both $ZnF_{16}Pc$ and light are present, which is the hallmark of PDT-induced phototoxicity.

Figures 8A, 8B, 8C, 8D, 8E, 8F:
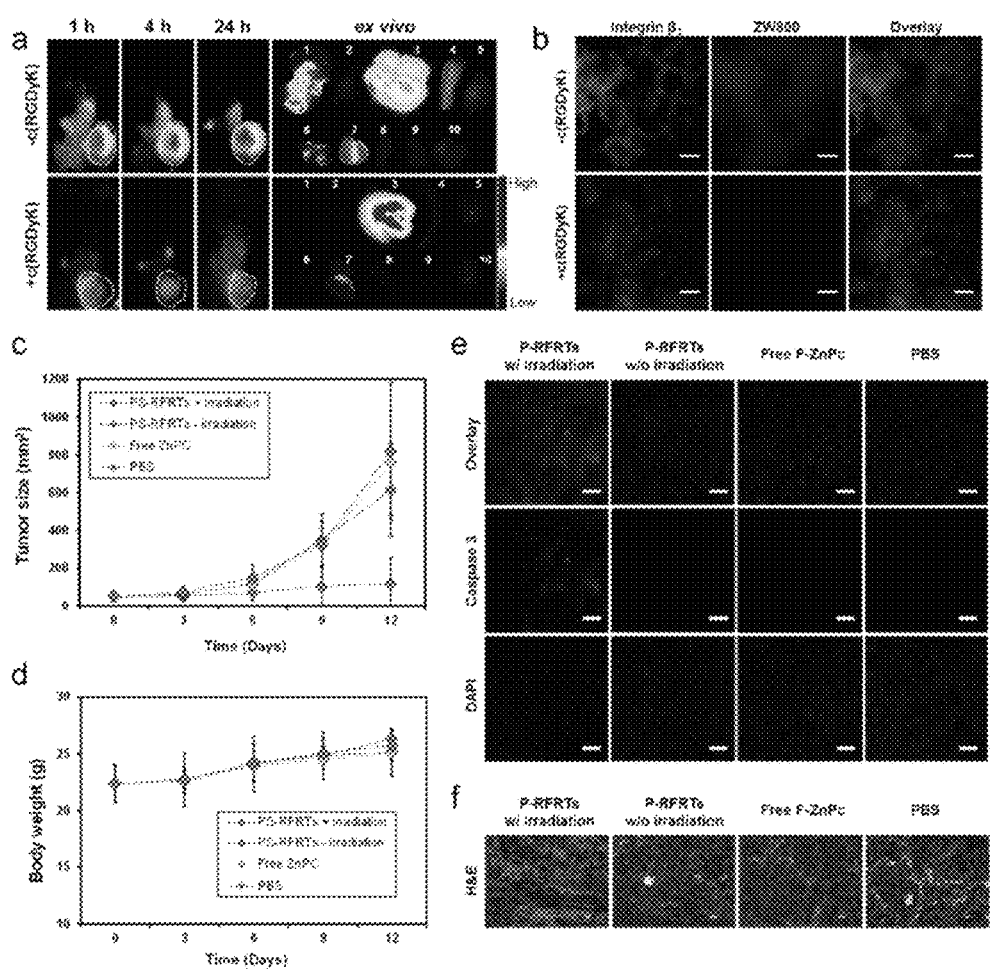
FIGS. 8A-8F are two graphs and four pictures illustrating the results from fluorescence imaging.
Figure 9:
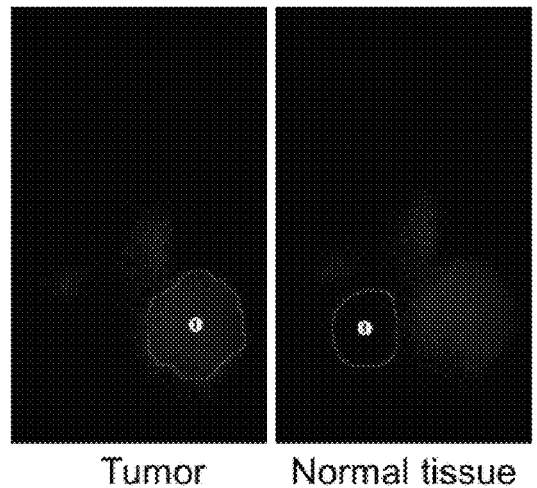
FIG. 9 is a representative image showing the selection of tumor and normal tissue on the in vivo images.

The tumor selectivity of P-RFRT in subcutaneous (s.c.) U87MG tumor models was studied. ZW800-labeled P-RFRTs (5 mg RFRTs/kg) was injected intravenously (i.v.) and fluorescence images on a Maestro scanner using an "orange" filter (640 to 820 nm) at different time points were acquired. Tumor-to-normal tissue (T/N) ratios were shown to be 3.82±0.56, 14.47±1.69, and 26.82±4.07 at 1, 4, and 24 h time points, respectively, demonstrating tumor accumulation (FIG. 8A and FIG. 9). When c(RGDyK) (30×) was injected prior to the PRFRT injection, the tumor uptake was significantly diminished. This confirms that tumor accumulation was mainly mediated by RGD-integrin interaction. Post-mortem ex vivo imaging was performed with tumors and other major organs (FIG. 8A). In addition to accumulation in the tumors, a high level of fluorescence activity in the liver was also found, which is common for a nanoparticle-based drug formulation. The uptake in other organs was much lower. The particle distribution in tumors was illustrated by immunofluorescence staining using an anti-integrin β3 antibody (FIG. 8B). Positive β3 staining was observed on both tumor vasculature and tumor cells. The ZW800 signals overlapped well with the positive β3 staining, conforming that the tumor retention was mainly caused by RGD-integrin interactions.

The treatment efficacy of P-RFRTs on a s.c. U87MG tumor model was studied. P-RFRTs (1.5 mg $ZnF_{16}Pc$/kg) was i.v. injected into the animals and the tumor surface over a 1 cm diameter beam spot (0.3 W/cm$^2$, 15 min) was illuminated (671 nm) 24 h after the injection (n=5). The three control groups were (1) P-RFRTs (1.5 mg $ZnF_{16}Pc$/kg, without irradiation); (2) free $ZnF_{16}Pc$ (1.5 mg $ZnF_{16}Pc$/kg, with irradiation); and (3) PBS (without irradiation). Tumor growth was similar in all the control groups but was significantly suppressed in the treatment group (FIG. 8C). On day 12, an average tumor inhibition rate (TIR) of 83.64% from the treatment group and found no impact on animals' body weights (FIG. 8D). After therapy, the mice were sacrificed and the tumors dissected for histology studies. The apoptosis level in the tumors was examined by caspase 3 staining. Positive staining with the samples from the treatment group but not with those from the controls (FIG. 8E) was found. Also, H&E staining demonstrates densely packed neoplastic cells in the controls but markedly disturbed tumor architecture in the treatment group (FIG. 8F). These observations agree with the therapy results. To demonstrate the size effects, caspase 3 staining with the skin and H&E staining with other normal organ tissues (e.g., the skin, heart, liver, spleen, lung, kidneys, intestine, muscle, and brain) was performed. No abnormalities were observed (FIGS. 10A and 10B), confirming that P-RFRT has minimal off-target damage.

Several observations confirm that $ZnF_{16}Pc$ is mostly loaded into the interiors of the RFRT nanocages: First, the nanoparticle size was almost unchanged after the $ZnF_{16}Pc$ loading, as shown by AFM. Second, $ZnF_{16}Pc$ is unloaded by the decomposition of the nanocarriers, either by reducing the pH or by inducing PDT. Third, P-RFRTs kept the targeting specificity against integrin αvβ3. This was confirmed by both in vitro and in vivo imaging studies. Fourth, preincubating RFRTs with Cu(II) can significantly suppress the loading of $ZnF_{16}Pc$ (from 60 to 25 wt %, Table 1). This indicates that most $ZnF_{16}Pc$ is competing for the same binding sites as Cu(II). The latter is mainly encapsulated into the interiors of RFRTs.

Figures 10A, 10B:
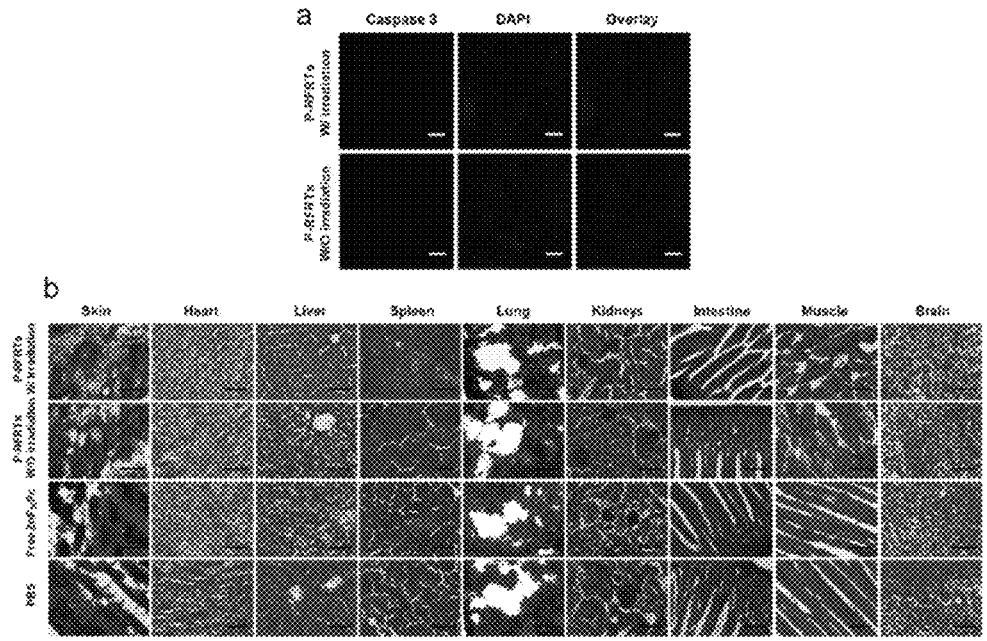
FIGS. 10A-10B are images of caspase stained and H&E stained tissues.
Figure 11:
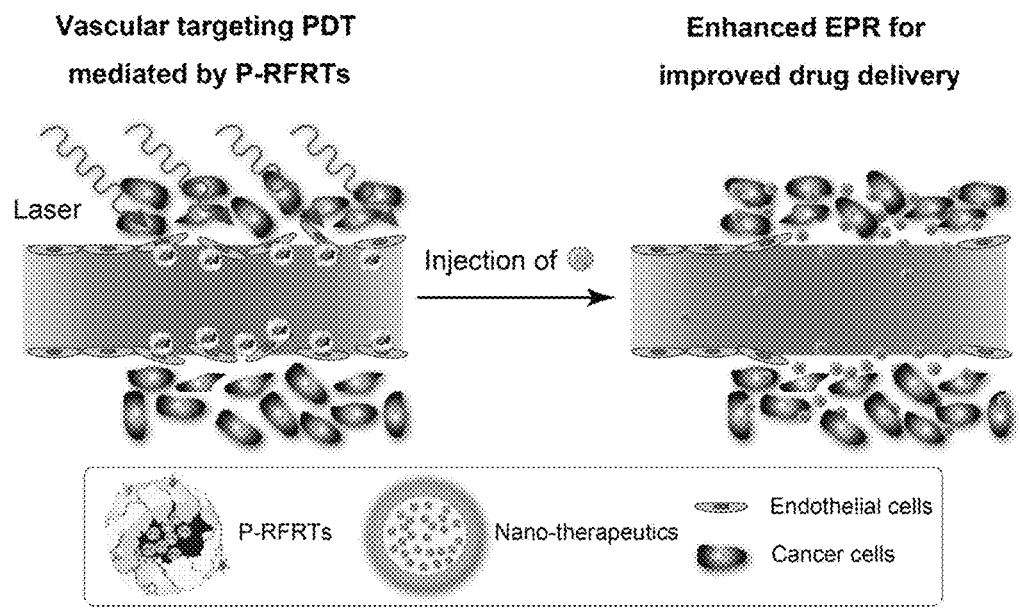
FIG. 11 is a scheme showing the working mechanism of P-RFRT-mediated PDT for enhanced delivery of nanoparticles to tumors. P-RFRTs are first injected and home to tumor endothelium through RGD-integrin interactions. With irradiation at an appropriate fluence rate, the procedure generates $^1O_2$ that acts on the endothelium. This leads to enlarged or newly formed endothelial gaps. Due to the increased leakiness, nanoparticles injected subsequently will extravasate and accumulate more efficiently at tumors.

$ZnF_{16}Pc$ was delivered by RFRTs to both tumor vasculature and U87MG tumor cells through RGD-integrin interactions (FIG. 8B). Hence, both mechanisms play a role in the tumor destruction. One issue of PDT is skin toxicity. However, negligible skin accumulation with P-RFRTs was found; instead, many of them were accumulated in the liver. In the context of PDT, however, uptake by the liver is a minor concern given its deep location and, hence, limited accessibility by light. Indeed, histology studies confirmed that the treatment caused little impact to the liver, as well as to other major organs (FIG. 10B). In the current study, $ZnF_{16}Pc$ at 1.5 mg/kg was injected and the tumors was irradiated at a fluence rate of 0.3 W/cm$^2$ for 15 min. Similar conditions were used in the previous studies. Given that no adverse effects were observed, it is possible to increase the dose to improve the treatment. It is also possible to improve the efficacy by adjusting the fluence and fluence rate.

Example 2: Tumor Vasculature Targeted Photodynamic Therapy for Enhanced Delivery of Nanoparticles A photodynamic therapy (PDT)-based method that can selectively increase vessel leakiness in tumors, linked to enhanced EPR effect is disclosed herein. For example, RGD modified ferritin (RFRT) was used as photosensitizer carriers. Ferritin was grown artificially with no iron feeding to afford a central cavity that can encapsulate metals or metal-containing compounds with high efficiency. In particular, $ZnF_{16}Pc$, a potent PS (λmax: 671 nm; ΦΔ: 0.85 in tetrahydrofuran), was encapsulated into RFRTs by up to 60 wt %. After systemic administration, $ZnF_{16}Pc$-loaded RFRTs (P-RFRTs) can home to the endothelium of neoplastic vessels via RGD-integrin interactions. This, in conjugation with photoirradiation at a low fluence rate, can permeabilize vasculature in tumors. The notion was confirmed in 4T1, U87MG, MDA-MB-435S, and PC-3 tumor xenograft models using albumins, quantum dots, and iron oxide nanoparticles. The treatment can increase tumor accumulation of nanoparticles by as much as 17.8-fold, while causing no adverse effects to normal tissues. Using Doxil as a representative nanoparticle drug, the impact of the procedure on cancer treatment was demonstrated. While exerting little cytotoxic power itself, P-RFRT-mediated PDT can improve the treatment efficacy of Doxil by 75.3%, which was attributed to the enhanced EPR effect.

Cell Culture.

4T1 (murine breast cancer), U87MG (human glioblastoma), PC-3 (human prostate cancer) and MDA-MB-435S (human melanoma) cell lines were purchased from ATCC. 4T1 and PC-3 cells were grown in RMPI 1640 medium supplemented with 10% fetal bovine serum (FBS) and 1% penicillin and streptomycin (MediaTech, USA). U87MG cells were grown in DMEM medium containing 10% FBS, 1% non-essential amino acids, and 1% penicillin and streptomycin. These three cell lines were incubated humidity under 37° C. and 5% $CO_2$. MDA-MB-435S cells were grown in the same medium as 4T1 and PC-3 but were incubated without $CO_2$.

Ferritin Purification and $ZnF_{16}Pc$ Loading.

The protocols for producing RFRTs and loading $ZnF_{16}Pc$ onto them have been reported (Zhen, Z., et al., ACS Nano 7, 6988-6996, 2013). For IR Dye800 labeling, P-RFRTs were incubated with IRDye800 for 30 min and purified through a NAP-5 column to remove uncoupled dye molecules. A starting ratio of 2:1 (IRDye800 to RFRTs) was used. The coupling efficiency was assessed spectroscopically by comparing with a predetermined standard curve (by monitoring absorbance at 780 nm). It was determined that the final conjugates have on average one IRDye800 per particle.

Animal Models.

Animal models were established by subcutaneous injection of ~10$^6$ cancer cells (4T1, PC-3, MDA-MB-435S and U87MG) to either one side or both sides of the hind limbs of 5-6 week athymic nude mice (Harlan). For 4T1 tumor models, the in vivo studies were conducted 1 week after the inoculation when the tumors reached a size of ~100 mm$^3$. For PC-3, MDA-MB-435S and U87MG tumor models, the in vivo studies were conducted 3 weeks after the inoculation when the tumors reached a size of ~100 mm$^3$. All the animal studies were according to a protocol approved by the Institutional Animal Care and Use Committee (IACUC) of University of Georgia.

Tumor Targeting with P-RFRTs.

For tumor targeting studies, IRDye800 labeled P-RFRTs (0.75 mg $ZnF_{16}Pc$/kg) were i.v. injected to bilateral 4T1 tumor models (n=5). Whole body fluorescence images were acquired on a Maestro II imaging system (PerkinElmer) using NIR emission filter (750-940 nm) up to 24 h post the injection. After the 24 h imaging, the animals were euthanized. The tumors as well as major organs were harvested for ex vivo imaging and histology studies.

EPR Enhancement Studies by Fluorescence Imaging.

For EPR enhancement studies, the animals were i.v. injected with P-RFRTs (0.75 mg $ZnF_{16}Pc$/kg) first (n=3). For bilateral tumor models, the right-side tumors were irradiated by a 671 nm laser (~1-cm diameter beam) for 30 min. The left-side tumors were shielded by aluminum foil and served as the control. For single-tumor models, two control groups (n=3) received P-RFRTs but not irradiation and PBS only. The fluence rates were measured by a laser power meter (FieldMax II, Coherent), and were varied (3, 8, 14, and 22 $mW/cm^2$). IRDye800 labeled HSA (0.5 mg/kg) was administered 5 min after the end of the 30 min irradiation. The animals were then subjected to fluorescence imaging on Maestro II using an NIR emission filter (750-940 nm). After 24 h imaging, the animals were sacrificed. The tumors as well as major organs were harvested for ex vivo imaging and histology studies. Uptake in a given organ was quantified by region of interest (ROI) analyses on both in vivo and ex vivo imaging results using the software provided by the vendor. The studies with QDs (Invitrogen, ex/em: 405-665/705 nm) were conducted in bilateral 4T1 tumor models (injected at 30 pmol per mouse). The procedures were similar to those with HSA except that the animals were sacrificed 1 h after the injection due to the short circulation half-lives of QDs.

EPR Enhancement Studies with IONPs.

The studies were conducted in bilateral 4T1 tumor models. The animals were i.v. injected with P-RFRTs (0.75 mg $ZnF_{16}Pc$/kg) first (n=3). The right-side tumors were irradiated 24 h later by a 671 nm laser (14 $mW/cm^2$, over a ~1-cm diameter beam) for 30 min. The left-side tumors were shielded by aluminum foil and served as the control. 5 min after the end of the irradiation, IONPs (Ocean Nanotech) at a dose of 10 mg Fe/kg were i.v. injected. T2-weighted FSE images were acquired on a 7 T Varian small animal MRI system before and 4 h and 24 h after the particle injection. The following parameters were used for the scans: TR=2.5 s; TE=48 ms; ETL=8; FOV 402 $mm^2$; matrix size=2562; 13 axial slices with 1 mm slice thickness. After the 24 h scan, the mice were sacrificed. The tumors were collected and snap-frozen for Prussian blue staining.

In Vivo Therapy Studies.

The therapy studies were performed in 4T1 tumor models (one tumor each animal). Briefly, 30 4-6 week female nude mice were subcutaneously injected with ~$10^6$ 4T1 cells to the right hind limb. The 30 mice were randomly divided to 6 groups, 5 mice each group. The study started 5 days after the inoculation (average tumor size of 50.68±18.79 $mm^3$). For treatment group, the animals were i.v. injected with P-RFRTs first (0.75 mg $ZnF_{16}Pc$/kg). The tumors were irradiated 24 h later by a 671 nm laser (14 $mW/cm^2$, over a ~1-cm diameter beam) for 30 min. Doxil were i.v. injected 5 min after the end of the irradiation at a dose of 10 mg/kg. The five control groups are: 1) receiving P-RFRTs and Doxil, but no irradiation; 2) Doxil only; 3) PBS and irradiation, no P-RFRTs and Doxil; 4) PBS only; and 5) P-RFRTs and irradiation, no Doxil. The tumors sizes and body weights were measured every other day. Tumor sizes were measured by a caliper, and computed following the formulation: size $(mm^3)$=length (mm)×width $(mm)^2$/2.

Immunofluorescence Staining.

The cryogenic slides were fixed with cold acetone for 30 min, washed by running water for 5 min, and blocked by 10% goat serum for 1 h. Anti-integrin β3 (ab75872, Abcam) or phycoerythrin-labeled anti-CD31 (ab25644, Abcam) antibodies were incubated with the slides at 4° C. overnight. Cy5.5-labeled secondary antibodies (ab6564, Abcam) were then added and incubated with the slides at 37° C. for 1 h. After gently rinsing with PBS, the slides were mounted and ready for microscopic imaging. TUNEL assays were performed by following a protocol provided by the vendor (FITC-labeled POD, GenScript).

Scanning Electron Microscopy.

Tumor blocks were cut into 10 μm slices. Those slices were mounted on coverslips, and fixed by 0.5% paraformaldehyde at 4° C. for 48 hours. For dehydration, ethanol of gradient concentrations (25%, 50%, 75%, 90% and 100%) was applied to the slices at room temperature, 30 min for each step. These slides were then sputter-coated with a gold/palladium mix after critical point dried in a SAM-DRI-790 CPD33, and then analyzed using a field emission gun SEM (FEI INSPECT F FEG-SEM).

Hematoxylin and Eosin Staining.

H&E staining was performed according to a protocol provided by the vendor (BBC Biochemical). Cryogenic slides (8 μm) were prepared and fixed with 10% formalin for about 30 min at room temperature. After washing with running water for 5 min, the slides were treated with gradient concentrations of alcohol (100, 95, and 70%), each for 20 s. The hematoxylin staining was performed for about 3 min and washed with water for 1 min. The eosin staining was performed for about 1 min. The slides were washed, treated with xylene, and mounted with Canada balsam. The images were acquired on a Nikon Eclipse 90i microscope.

Figures 12A, 12B, 12C:
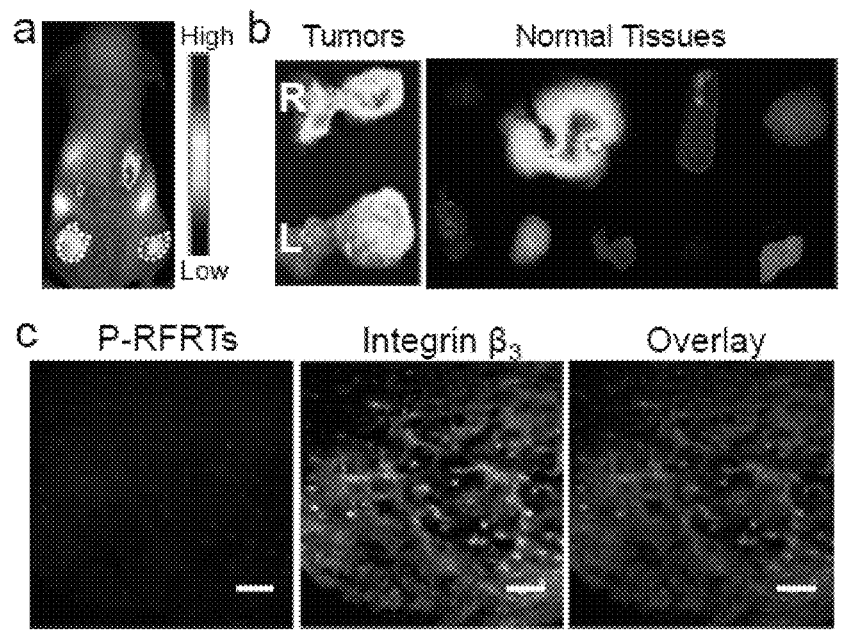
FIGS. 12A-12C are images showing tumor targeting of P-RFRTs.
Figure 13:
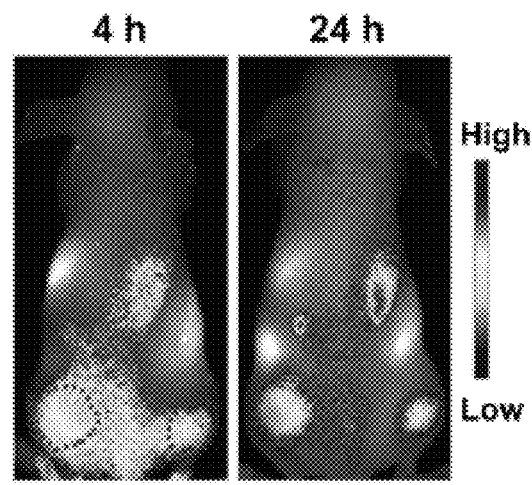
FIG. 13 contains images from a tumor targeting study with P-RFRTs in bilateral 4T1 tumor models. The tumors were circled by dashed lines.

Tumor Targeting with P-RFRTs:

The tumor targeting efficiency of P-RFRTs in bilateral 4T1 (murine breast cancer) tumor xenograft models (n=5) was demonstrated. To facilitate the tracking, P-RFRTs were labeled with IRDye800 (ex/em: 780/800 nm, Licor). These labeled P-RFRTs (0.75 mg $ZnF_{16}Pc$/kg) were intravenously (i.v.) injected, and their migration was studied by fluorescence imaging on Maestro II. Accumulation of signals in both left and right tumors were observed (FIGS. 12A and 13). At 24 h, the average tumor-to-normal (T/N) tissue ratio was 94.51 (97.52±10.60 and 91.50±13.00 for left and right tumors, respectively; FIGS. 12A and 12B), indicating high tumor selectivity. Immunofluorescence staining on tumor sections revealed a correlation between the P-RFRTs distribution and positive integrin β3 staining, demonstrating that the targeting was mainly mediated by RGD-integrin interactions (FIG. 12C). Notably, 4T1 cells express a relatively low level of integrin αvβ3 on the surface. Many of the P-RFRTs, therefore, were positioned on tumor vessels instead of tumor cells at 24 h (FIG. 12C).

Evaluating the EPR Enhancement Effect with Albumins:

Using human serum albumins (HSA) as drug mimics, the impact of P-RFRT-mediated PDT on the EPR effect was studied. HAS has a molecular weight of ~65,000 and a diameter of ~7 nm. The study was comprised of two steps. In the first step, P-RFRTs (0.75 mg $ZnF_{16}Pc$/kg) were i.v. administered (n=3), followed by photoirradiation by a 671 nm laser at 24 h. The laser was given in the form of a 1-cm beam that covers the right-side tumor of an animal. The left-side tumors were not irradiated and served as controls. A fluence rate of 14 $mW/cm^2$ (for 30 min) was applied, which was much lower than the power used in conventional PDT (50-300 mW/cm$^2$). In the second step, IRDye800-labeled HSA (1 mg/kg) was i.v. injected 5 min after the end of the laser irradiation. The animals were then subjected to fluorescence imaging, and the accumulation of probes in the left- and right-tumors was compared.

Figures 14A, 14B, 14C, 14D:
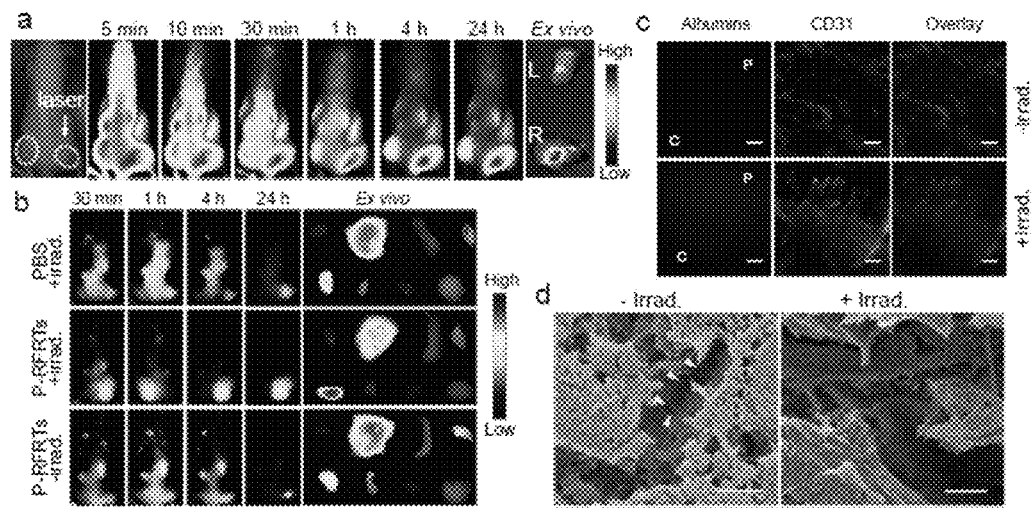
FIGS. 14A-14D show the study of EPR enhancement with albumins.

At all the time points examined, there was significantly higher uptake of probes in the right-side tumors (FIG. 14A). By region-of-interest (ROI) analysis, the relative increase of tumor uptake (RIU) was quantified and compared which is the ratio of fluorescence readings between the right and left tumors. At 1, 4, and 24 h, RIU was 1.88±0.29, 2.23±0.34, and 2.96±0.27, respectively. After the 24 h imaging, the animals were euthanized and the tumors were harvested. The ex vivo imaging with tumors revealed a similar level of difference in uptake between the irradiated and un-irradiated tumors (FIG. 14A). The enhanced tumor uptake by PDT was further assessed by microscopy studies (FIG. 14A). Interestingly, in addition to overall increased uptake, there is also a change in the distribution pattern of the albumins: In un-irradiated tumors, the albumins were found only in the tumors' peripheries; in irradiated tumors, on the other hand, albumins penetrated much deeper into the masses.

Figure 15:
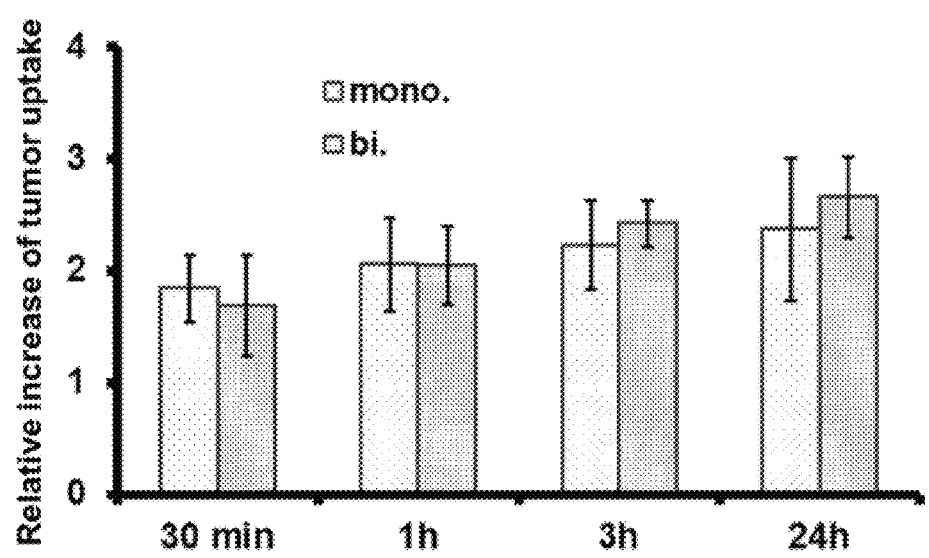
FIG. 15 is a graph of relative increase of tumor uptake. The results came from studies performed on 4T1 tumor models bearing either one (mono) or two (bi) tumors.

To confirm the enhancement effect, similar studies in 4T1 tumor models which bear one tumor each were conducted. The tumors were treated by the same injection and irradiation procedures (14 mW/cm$^2$ for 30 min at 24 h after P-RFRT injection), followed by albumin administration (IRDye800 labeled, 1 mg/kg). In the two control groups, animals received P-RFRTs but no irradiation, or irradiation only, before albumin injections. Compared to the controls, increased tumor accumulation was observed in the PDT-treated animals (FIG. 14C). At 24 h, an increased uptake of 2.41±0.39 fold was observed between the irradiated and un-irradiated groups, amplitude that is comparable to that observed in bilateral tumor models. As a matter of fact, comparable RIU values between the two sets of studies were observed at all time points (FIG. 15).

The harvested tumors and normal tissues were then subjected to ex vivo imaging (FIG. 14C). There was no significant difference in albumin accumulation in normal tissues among the three groups. This demonstrates that the PDT treatment is highly selective. Aside from increasing tumor uptake, it has little impact on the delivery of albumins to other organs.

Figure 16:
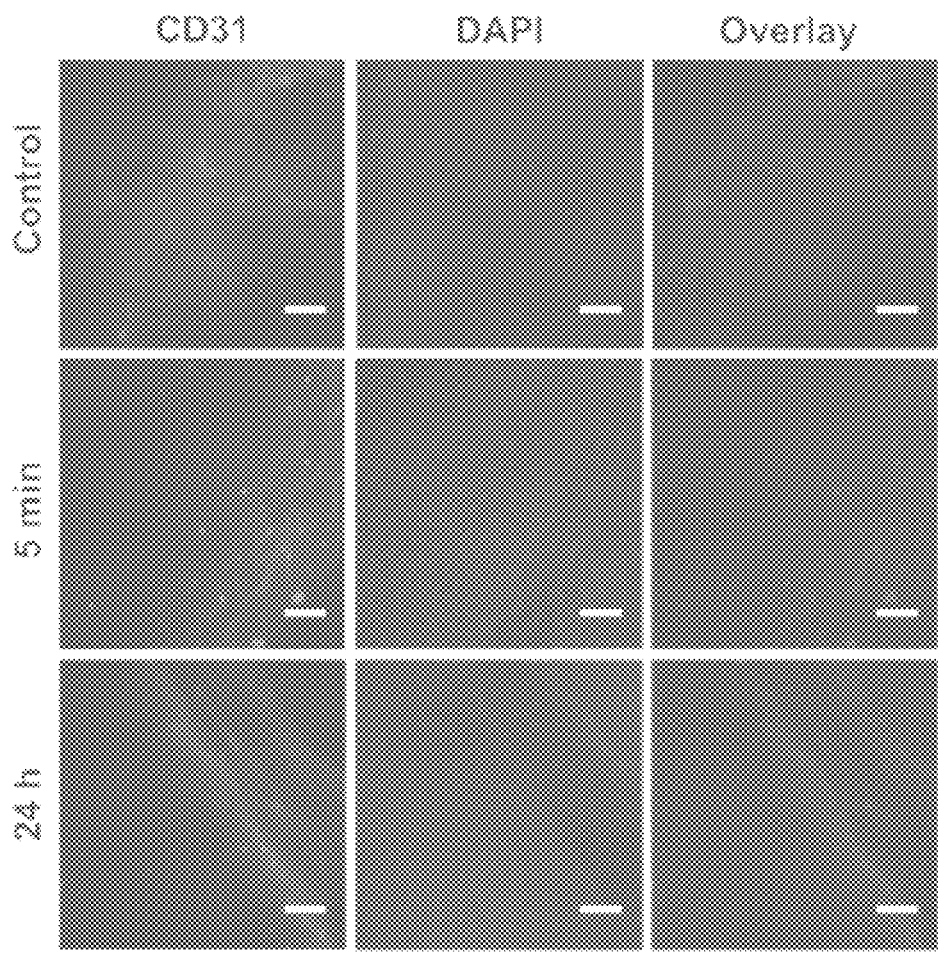
FIG. 16 shows CD31 staining on 4T1 tumor samples taken before (the first row) as well as 5 min and 24 h after P-RFRT-mediated PDT. Red, CD31. Blue, DAPI. Scale bars, 100 µm.

To elucidate the mechanism behind the uptake increase, in a separate study, animals were sacrificed 5 min after the end of irradiation (without injection of albumins), then the tumors were harvested for scanning electron microscopy (SEM) analysis. Compared to the un-irradiated tumors, many more large fenestrae on the endothelial walls of the irradiated ones were observed (FIG. 14D, highlighted by red arrows). The yielded vessels are thus more permeable, which is believed to be the primary cause behind the enhanced tumor uptake. Changes were also found on the luminal microstructures after the PDT. Without irradiation, the lumen of vessels was enriched with branched lining cells, which formed extensive bridges and tunnels (FIG. 14D, highlighted by yellow arrows). These features are commonplace in poorly developed tumor vessels. In contrast, tumors that had undergone irradiation displayed much smoother vessel surface (FIG. 14D), indicating a possible plumbing function of the PDT procedure. This hypothesis is corroborated by immunofluorescence microscopy on tumors before as well as 5 min and 24 h after the PDT (FIG. 16). Un-treated tumors featured irregular and convoluted vessels, which correlate with the SEM observations. After the PDT treatment, however, the blood vessels become more regular and ordered, probably more so at 5 min (FIG. 16).

Figure 17:
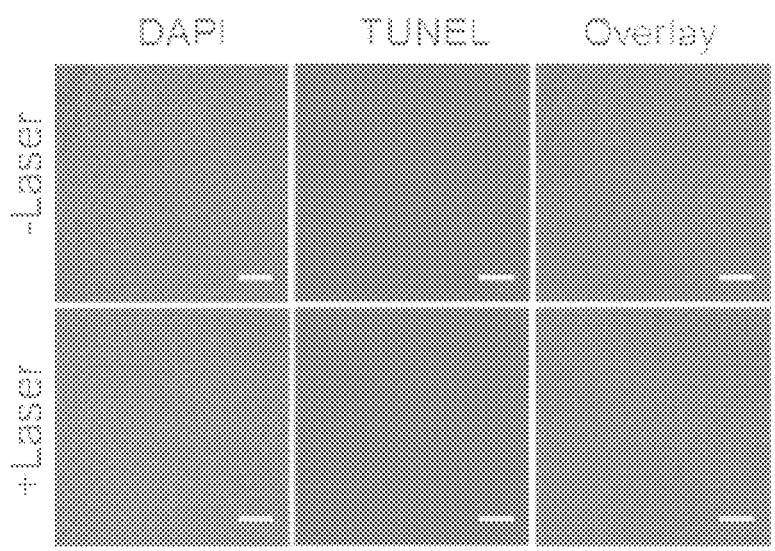
FIG. 17 shows results from TUNEL assays on samples from irradiated (PDT-treated) and non-irradiated (non-PDT treated) tumors. Blue, DAPI. Green, TUNEL. Scale bars, 100 µm.

The tumor samples were also subjected to TUNEL assays, which demonstrate the toxicity caused by PDT. Few cell deaths were detected in the PDT treated tumors (FIG. 17). This demonstrates that despite the vascular effects the PDT induced, its toxicity to the surroundings is minimal. This is attributable to the low fluence-rate used, and also, to the endothelium targeting capacity afforded by RFRTs. In combination, the $^1O_2$ generated acts as a gentle, local cleaning of the vessels, thereby avoiding the extensive vessel occlusion and destruction that is often observed in conventional PDT.

Figures 18A, 18B, 18C:
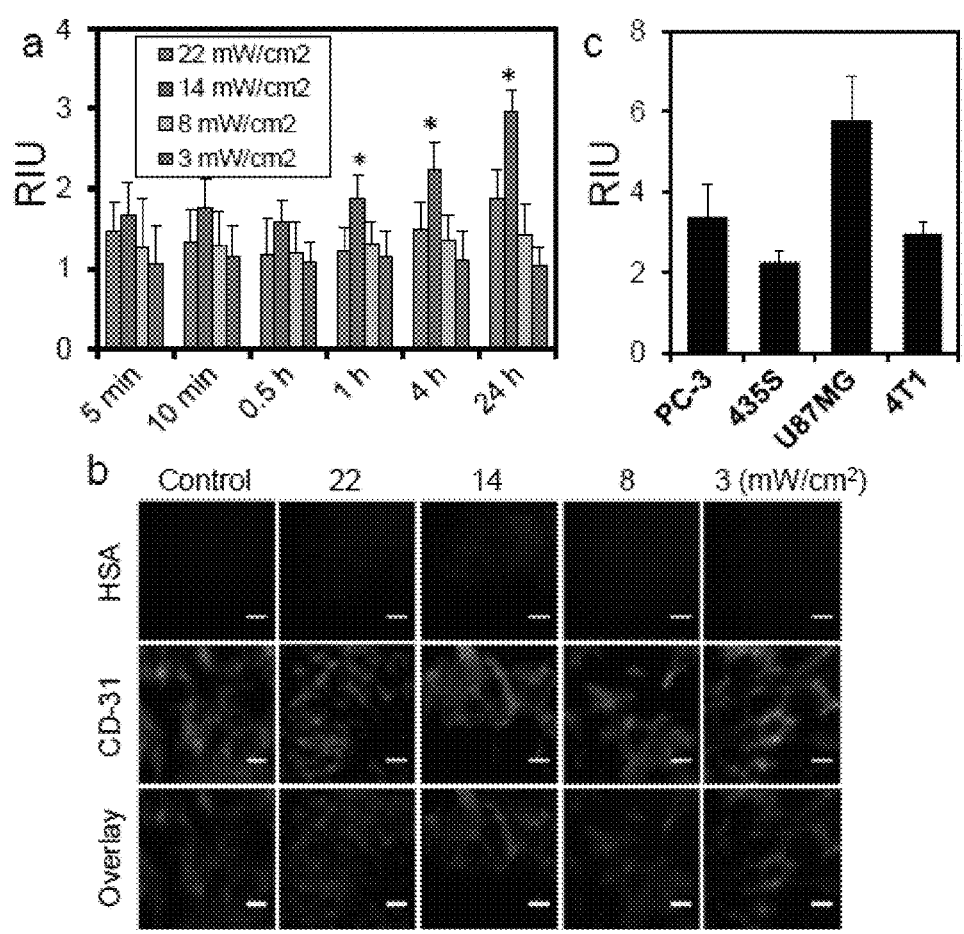
FIGS. 18A-18C show the effect of fluence rate on EPR enhancement.
Figures 19A, 19B:
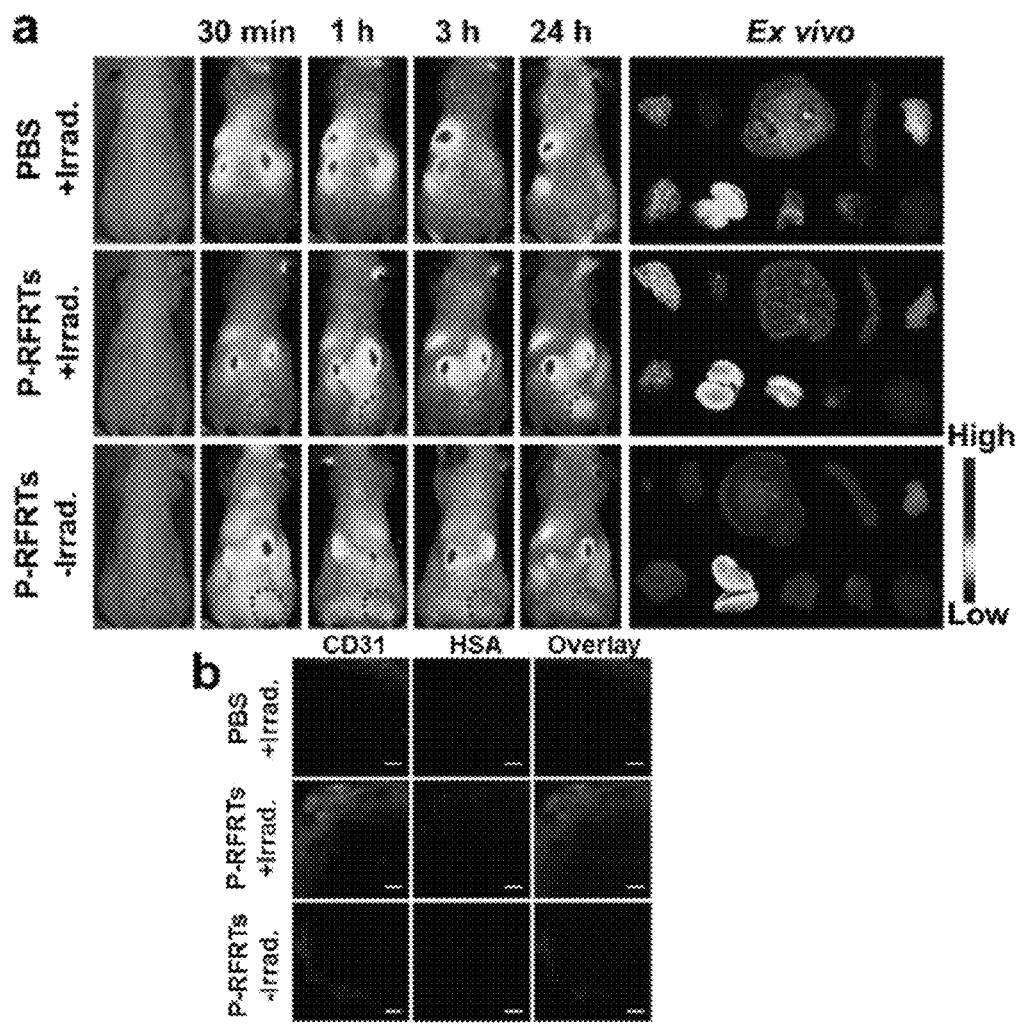
FIGS. 19A-19B are imaging and histology studies on tumor tissues.
Figures 20A, 20B:
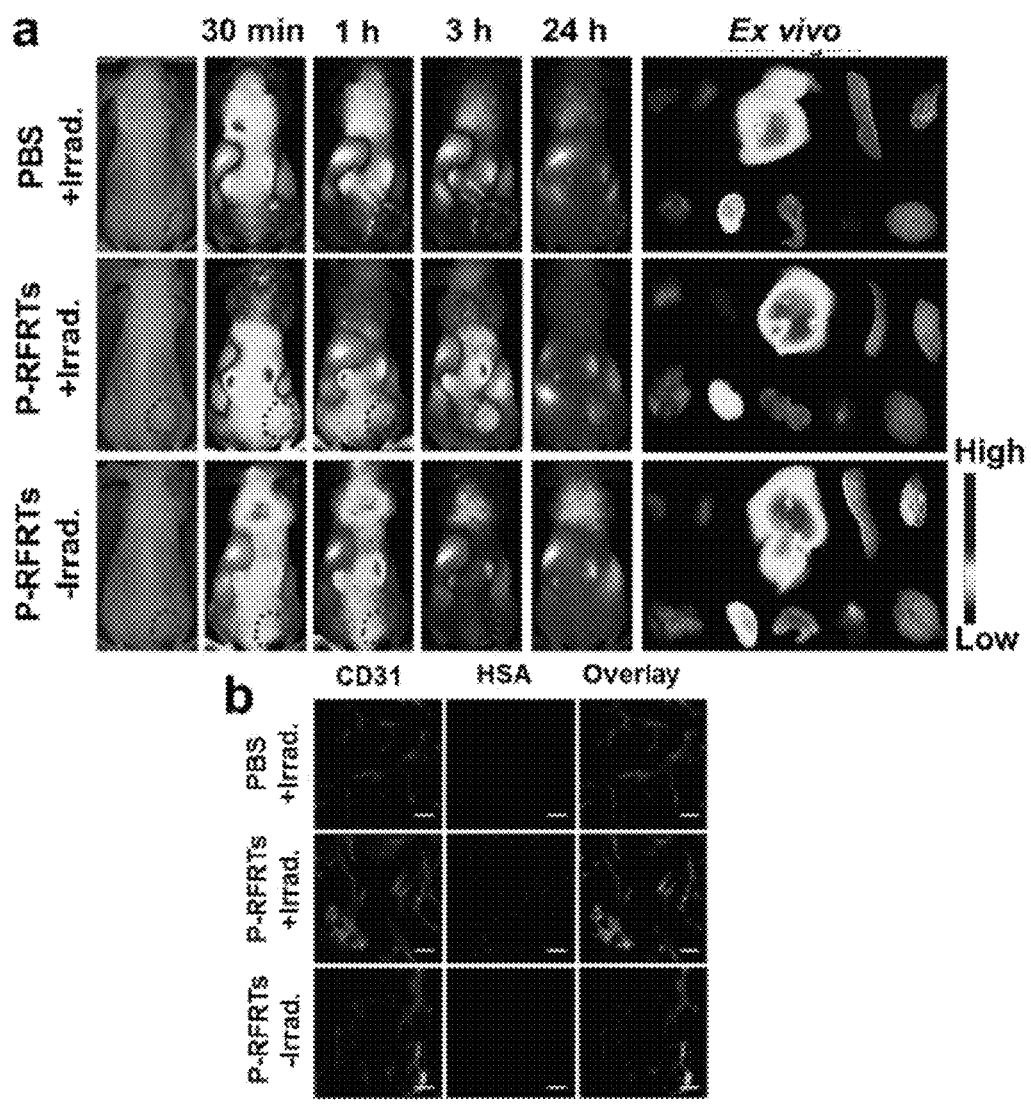
FIGS. 20A-20B are imaging and histology studies on tumor tissues.
Figures 21A, 21B:
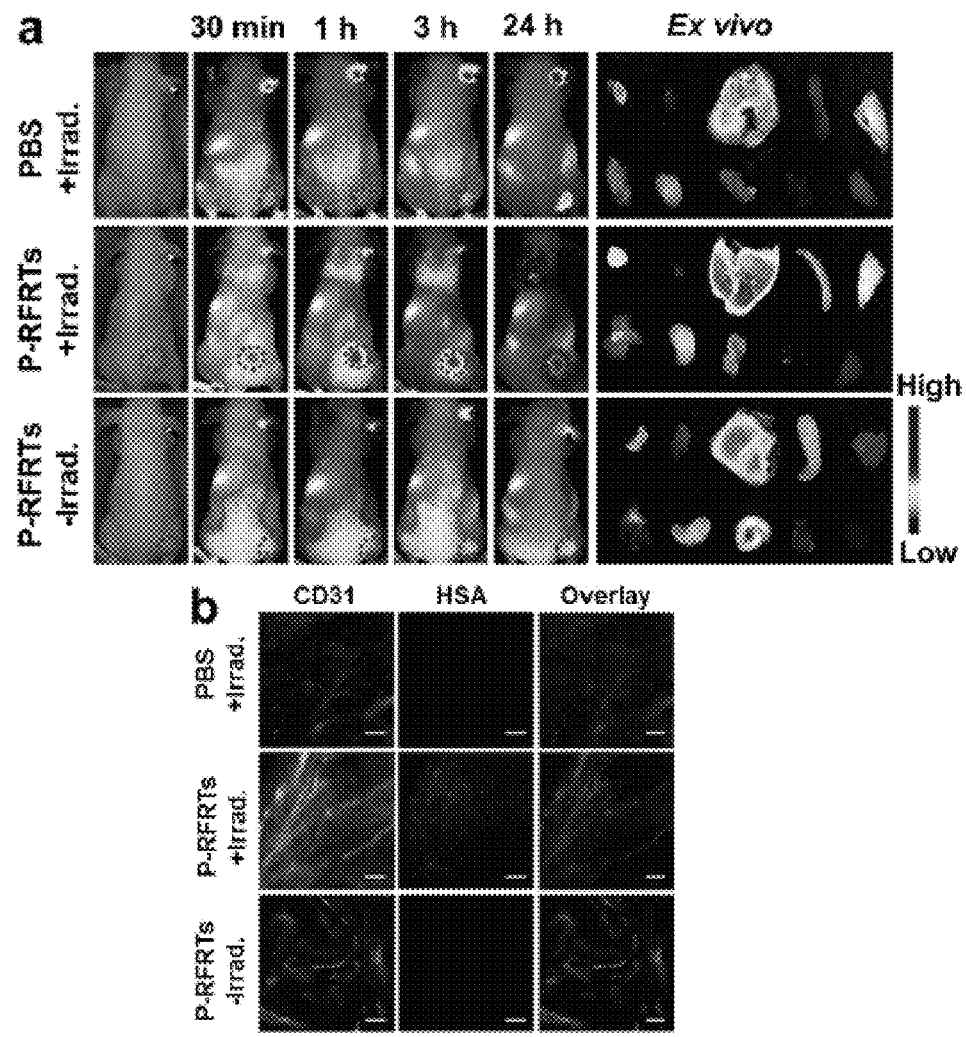
FIGS. 21A-21B are imaging and histology studies on tumor tissues.

Fluence-Rate Dependence of the EPR Enhancement:

To examine the dependence of the EPR effect on fluence rate, the preceding study was repeated with bilateral 4T1 tumor models but the fluence rates were varied (the illumination time was fixed at 30 min) RIU values from different irradiation conditions were then assessed and compared. At 3 mW/cm$^2$, there was almost no enhancement effect, showing an RIU value of 1.03±0.24 at 24 h (FIG. 18A). Increasing the fluence rate to 8 mW/cm$^2$ led to enhanced tumor uptake (1.43±0.38 at 24 h) but the amplitude was smaller than that at 14 mW/cm$^2$ (2.96±0.27). Further increasing fluence rate beyond 14 mM/cm$^2$ to 22 mW/cm$^2$ did not enhance the tumor uptake accordingly, showing a RIU value of 1.89±0.36 at 24 h (FIG. 18A). The difference in tumor uptake was better illustrated by immunofluorescence staining Compared to the control and other illumination conditions, the 14 mW/cm$^2$ group manifested the most prominent probe accumulation and dispersion (FIG. 18B). These results show that an increased fluence-rate is not always beneficial to the EPR enhancement. While too low a fluence rate can be insufficient to induce vessel permeabilization, a too high fluence rate can be overkill; possibly causing partial or complete occlusion of the vessel that adversely affects the nanoparticle delivery.

Figure 22:
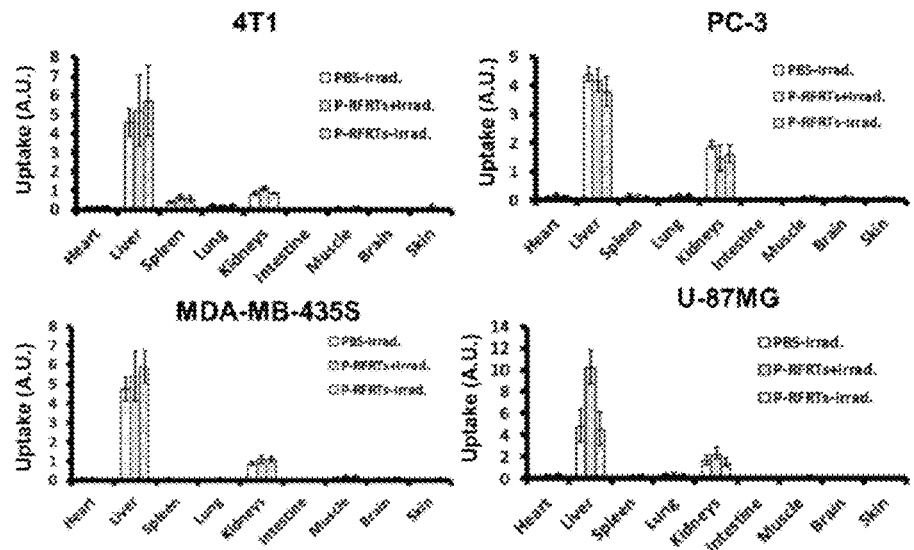
FIG. 22 is a histogram comparison of accumulation of albumins in normal tissues. The results were based on ROI analyses on ex vivo imaging data (from FIGS. 14C and 19-21).

EPR Enhancement in Different Tumor Models:

Using the same injection and irradiation plans, the EPR enhancement effect in other tumor models was demonstrated. These include PC-3 (human prostate cancer), MDA-MB-435S (human melanoma), and U87MG (human glioblastoma) tumor-bearing mice. In every model, enhanced accumulation of albumins in tumors after the PDT treatment was observed (FIGS. 18D and 19-21). Specifically, 24 h RIU values were 3.39±0.80, 2.27±0.27, and 5.79±1.10, respectively, for PC-3, MDA-MB-435S, and U87MG tumors. Similarly, the PDT treatment caused little change in distribution of albumins in normal tissues (FIG. 22). Notably, integrin αvβ3 is expressed moderately or abundantly on the surface of PC-3 (integrin $\alpha_v\beta_3^+$), MDA-MB-435S (integrin $\alpha_v\beta_3^{++}$), and U87MG (integrin $\alpha_v\beta_3^{+++}$) cells. Hence, some or a large amount of injected P-RFRTs homed to cancer cells in these models. The PDT effects on cancer cells do not affect the EPR enhancement, at least not adversely.

Figures 23A, 23B, 23C:
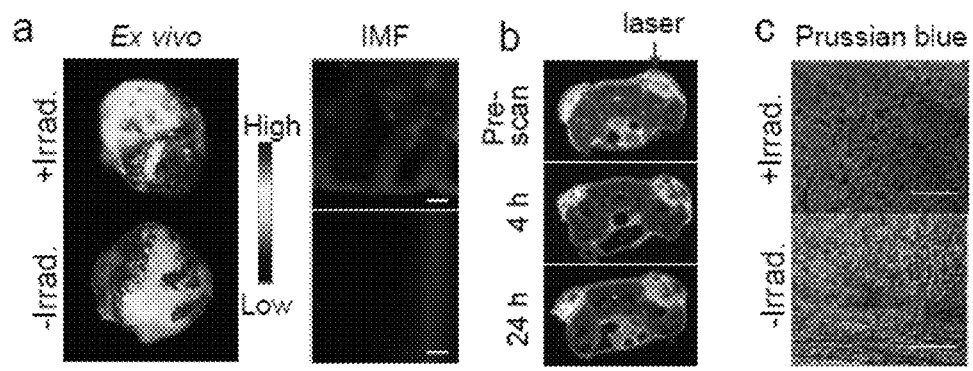
FIGS. 23A-23C show EPR enhancement with nanoparticles.

EPR Enhancement for QDs and IONPs:

To demonstrate that the disclosed methods apply to particles with a larger size, quantum dots (QDs, from Invitrogen, ex/em: 405-665/705 nm), which have a diameter of ~50 nm were used in the experiments. The study was performed on bilateral 4T1 tumor models. QDs were injected after P-RFRT mediated PDT (30 pmol/mouse, n=3). The contralateral tumor receiving no photo-irradiation served as the control. After 1 h, the animals were sacrificed and the tumors dissected for comparison by ex vivo imaging (FIG. 23A). A 1 h observation window was chosen because QDs have a much shorter circulation half-life than albumins. ROI analyses on ex vivo imaging with dissected tumors revealed a RIU of 17.8±4.8 between irradiated and un-irradiated tumors. This increase in the EPR enhancement over that found with albumins was attributed to the difference in particle dimensions. Due to the larger size of QDs, the endothelial lining represents a more difficult barrier for them than for albumins. Therefore, the PDT treatment, which lowers the threshold, works more effectively on QDs to improve their extravasation at the tumors. The difference may have been further augmented by the fact that large nanoparticles are less mobile, meaning that compared to albumins, QDs have a higher tendency to stay at the tumor interstitial space after the extravasation. This was supported by immunofluorescence staining, which found a large amount of QDs accumulated just outside the blood vessels (FIG. 23A). In contrast, albumins were disseminated much deeper from the vessels (FIG. 14B).

The PDT-based method also applies to iron oxide nanoparticles (IONPs). In a separate study, ~40 nm IONPs (core size~15 nm, Ocean Nanotech) as model nanoparticles were injected into bilateral 4T1 tumor models after the PDT (n=3). A commonly used MRI contrast probe, IONPs shorten T2 relaxation times of near-by protons, causing regional signal drop on T2-weighted MR maps. Compared to the un-irradiated side, many more signal voids were observed in the irradiated tumors, indicating an enhanced tumor accumulation (FIG. 23B). The result was further validated by Prussian blue staining, which found more iron deposits in tumors that had undergone irradiation (FIG. 23C).

EPR Enhancement for Improving Tumor Therapy with Doxil:

Therapy studies were evaluated in 4T1 xenograft tumor models (bearing one tumor each). Doxil, a liposome-based doxorubicin drug, was used as a nanoparticle therapeutic. Specifically, animals were injected with P-RFRTs first (0.75 mg/kg), followed by irradiation at 24 h (14 mW/cm$^2$ for 30 min). Right after the irradiation, Doxil (10 mg/kg) was i.v. administered (n=5). Several control groups were also studied. These include animals receiving P-RFRTs and Doxil but no irradiation, P-RFRTs and irradiation but no Doxil, Doxil only, irradiation only, and PBS only (n=5).

Figures 24A, 24B, 24C, 24D:
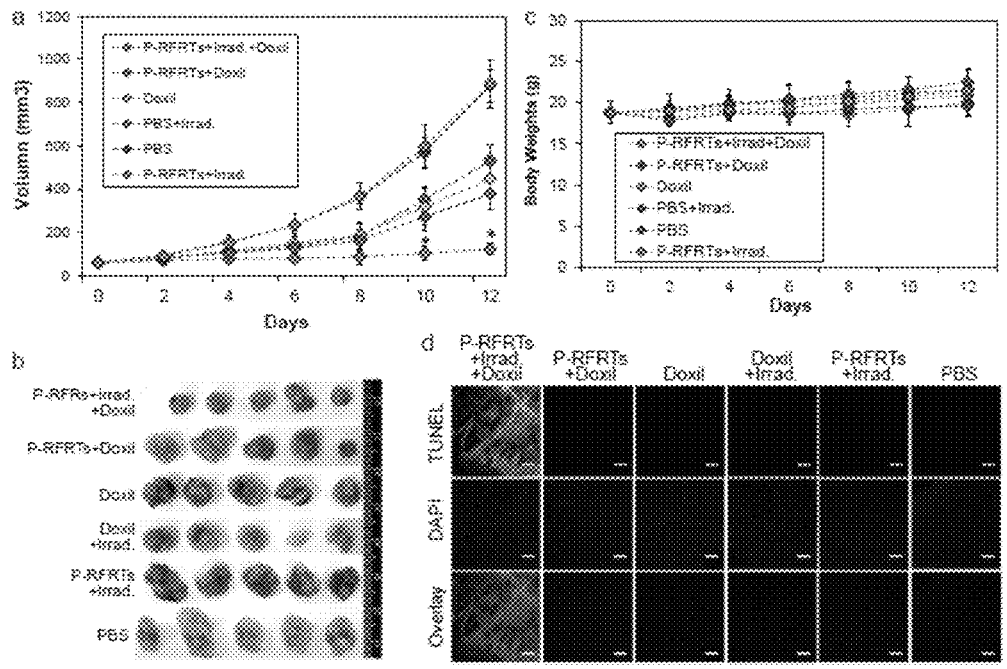
FIGS. 24A-24D show EPR enhancement for improved tumor therapy.

The group that received PDT only (P-RFRTs+Irrad.) showed a similar tumor growth rate to animals receiving only PBS (FIG. 24A). This indicates that PDT alone caused few therapeutic effects. The data correlates well with the observations from TUNEL assays (FIG. 17), which found little toxicity of PDT at this low fluence rate. Animals treated with Doxil and P-RFRTs (but without irradiation) and Doxil showed comparable but mediocre tumor suppression. On day 12, tumor growth inhibition (TGI) were computed to be 39.4% and 49.0% for these two groups, respectively (FIG. 24A). In contrast, significantly improved tumor growth inhibition was observed in animals receiving both PDT and Doxil (P-RFRTs+Irrad.+Doxil). The combination almost completely arrested tumor growth in the first week, including tumor shrinkage observed in two animals. On day 12, a TGI of 85.9% was observed. This represents an increased treatment efficacy by 75.3% compared to Doxil alone (FIG. 24A). Given that the PDT itself has no direct therapy contribution, the improvement must have been due to the enhanced EPR caused by the PDT.

Figure 25:
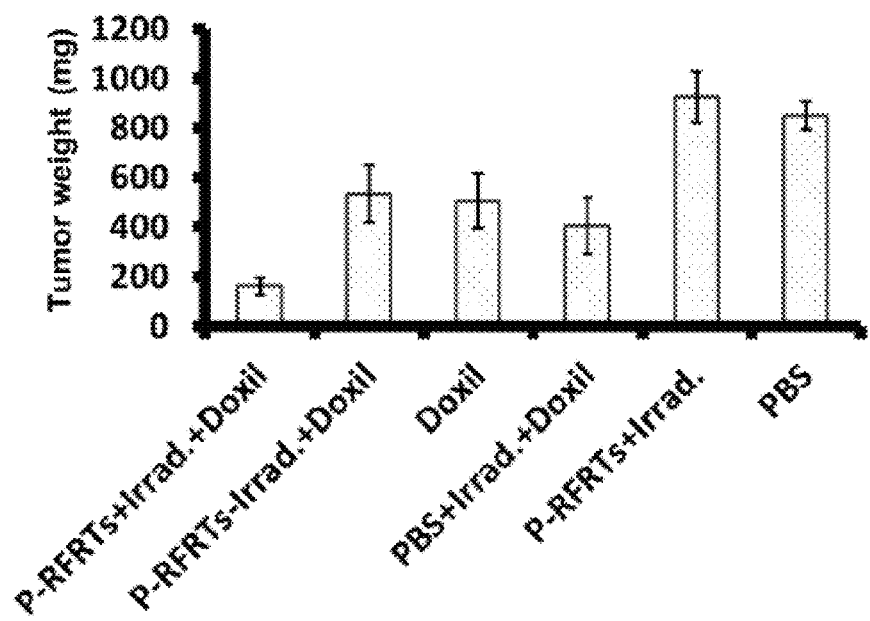
FIG. 25 is a histogram showing comparison of tumor weights among different therapy groups.
Figure 26:
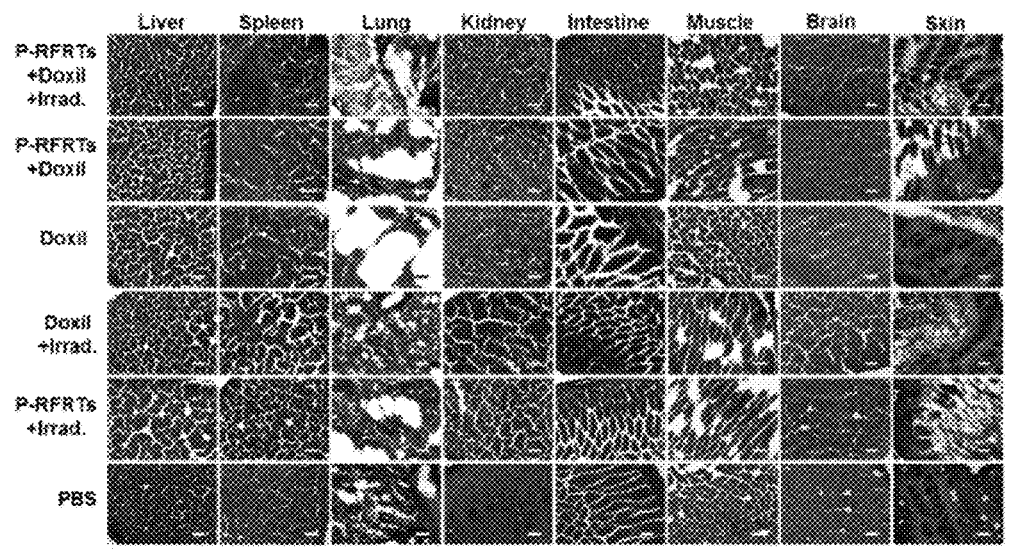
FIG. 26 shows H&E staining on normal tissues from different therapy groups. Scale bars, 100 µm.
Figure 27:
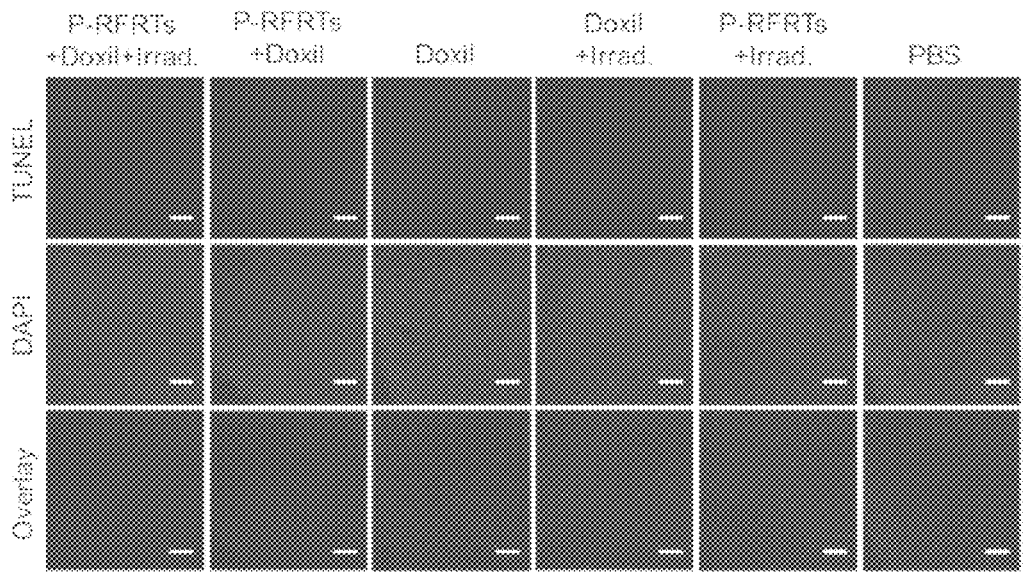
FIG. 27 is a TUNEL assays with heart tissue samples from different therapy groups. Blue, DAPI. Green, TUNEL. Scale bars, 100 µm.

After the therapy studies, the animals were sacrificed. The tumors were dissected and compared both visually (FIG. 24B) and by weight (FIG. 25). The results corroborate well with the measurements in FIG. 12A. TUNEL assays were also performed on the tumor tissues (FIG. 24C). A significantly higher level of cell death was observed in the group receiving PDT and Doxil combination. Otherwise, there was no sign of additional toxicity induced by the PDT (FIG. 26). These include no additional heart toxicity, which is commonly associated with Doxil-based treatments (FIG. 27). Also, there was no significant difference of body weights between the treatment group and other groups receiving Doxil (FIG. 24D). All these observations demonstrate that the PDT modulation is highly selective and of minimal contralateral damage.

The methods for PDT-induced vessel permeabilization, disclosed herein, are not accompanied by other vascular effects like vessel collapse and occlusion. Two factors are the irradiance rate and efficient and selective photosensitizer delivery means. In the clinic, vascular targeting is achieved through a passive approach that relies on distribution of photosensitizers in the tumor microenvironments. After systemic injection, the photosensitizer is firstly retained in the tumor vasculature, and then slowly diffused to tumor interstitial places or cellular compartments. Illuminating at an early time point, therefore, will confine the damage mostly within the vasculatures, and at a late time point mostly on cancer cells. However, taking verterpofin as an example, a drug-light interval of 15 min is regarded as mainly vascular targeting and that of 3 h as cellular targeting. This approach have clear limitations in the context of vessel permeabilization, poor tumor selectivity, photosensitizers are randomly distributed in the lumen of blood vessels at the time of illumination, not necessarily on or close to the endothelium. Since $^1O_2$ molecules have an extremely short lifetime (10-320 nanoseconds, or 10 to 55 nm in diffusion length), most do not survive to reach the endothelial walls. Instead, they act on nearby platelets/red blood cells, stimulating the release of thromboxane and generating thrombi. Overall, conventional PDT show comprehensive damage (collectively on platelets/red blood cells, endothelium, and cancer cells).

The disclosed compositions and methods are accumulated preferentially in tumors, with many of them stationed on the endothelium via RGD-integrin interactions. This high selectivity allows minimized contralateral damage and thrombus formation. The technology is also useful in the delivery of macromolecules to tumors, as demonstrated in the case of albumins.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A composition, comprising:
    an apoprotein cage comprising a metal binding site, and a therapeutic agent comprising a metal and a photosensitizer derived from a tetrapyrollic compound,
    wherein the therapeutic agent is encapsulated within the apoprotein cage, and
    wherein the composition comprises at least 10 wt % of the therapeutic agent.

2. The composition of claim 1, wherein the apoprotein cage is an apoferritin or an apoferritin-like cage.

3. The composition of claim 1, wherein the apoprotein cage is an apoferritin and the apoferritin is derived from a eukaryote.

4. The composition of claim 1, wherein the metal is selected from the group consisting of zinc, tin, aluminum, ruthenium, osmium, iron, rhenium, and technetium.

5. The composition of claim 1, wherein the tetrapyrollic compound is selected from a porphyrin, a phthalocyanine, an expanded pyrrolic macrocycle, or combinations thereof.

6. The composition of claim 1, wherein the photosensitizer is derived from a porphyrin and the porphyrin is selected from the group consisting of green porphyrins, tetrahydrochlorins, pyropheophosphides, purpurins, texaphyrins, phenothiaziniums, phthalocyanines, napthalocyanines, porphycenes, and pheophorbides.

7. The composition of claim 1, wherein the photosensitizer is selected from the group consisting of zinc phthalocyanine, sulfonated aluminum phthalocyanine, magnesium phthalocyanine, and zinc tetraphenyl porphyrin.

8. The composition of claim 1, wherein the composition further comprises a small molecule comprising a metal selected from the group consisting of copper, zinc, cobalt, titanium, zirconium, vanadium, molybdenum, niobium, platinum, tin, aluminum, ruthenium, osmium, iron, rhenium, technetium, gold, gallium, gadolinium, manganese, nickel, silver, palladium, cadmium, indium, and europium.

9. The composition of claim 1, wherein the composition further comprises an anti-cancer drug selected from the group consisting of doxorubicin, Methotrexate, Paclitaxel, Cisplatin, carboplatin, Nedaplatin, oxaliplatin, heptaplatin, lobaplatin, Bleomycin, docetaxel, gemcitabine, daunomycin, epirubicin, idarubicin, mitoxantrone, Valrubicin, Vorinostat, Gefitinib, Imatinib, and Actinomycin.

10. The composition of claim 1, wherein the composition further comprises a nanoparticle formulation of an anti-cancer agent.

11. The composition of claim 1, wherein the composition further comprises a macromolecule selected from the group consisting of Cetuximab, Panitumumab, Trastuzumab, Pertuzumab, Ado-trastuzumab emtansine, Bevacizumab, Ipilimumab, Rituximab, Ofatumubab, Alemtuzumab, Brentuximab vedotin, and Gemtuzumab ozogamicin.

12. The composition of claim 1, wherein the composition comprises from 10 wt % to 80 wt % of the therapeutic agent.

13. The composition of claim 1, wherein the composition further comprises a cell recognition moiety.

14. The composition of claim 13, wherein the cell recognition moiety is selected from the group consisting of a receptor, ligand, polynucleotide, peptide, polynucleotide binding agent, antigen, and antibody.

15. The composition of claim 13, wherein the cell recognition moiety is a peptide that has a length of from about 6 amino acids to about 25 amino acids.

16. The composition of claim 13, wherein the cell recognition moiety comprises SEQ ID NO:1.

17. The composition of claim 13, wherein the cell recognition moiety comprises an amino acid sequence that is greater than 75% identical to SEQ ID NO:1.

18. A pharmaceutical composition comprising: a) the composition of claim 1; and b) a pharmaceutically acceptable excipient.

19. A method for permeabilizing an endothelial lining of a cancerous tissue within a subject's body, the method comprising:
(a) administering to the subject a composition according to claim 1 for causing photodynamic or photothermal damage to the endothelial lining; and
(b) irradiating the subject at an effective fluence rate and for an effective period, thereby causing an increase in a Enhanced Permeabilization and Retention (EPR) effect without causing significant occlusion and/or vessel collapse to cancerous cells.

20. The method of claim 19, wherein the apoprotein cage is selected from the group consisting of apoferritin and apoferritin-like nanocage, heat shock proteins, lumazine synthase, and DNA-binding protein.

21. The method of claim 19, wherein the composition is administered intravenously.

22. The method of claim 19, wherein the composition is administered topically.

23. The method of claim 19, wherein the cancerous tissue is selected from the group consisting of ovarian cancer, colorectal cancer, breast cancer, bladder cancer, brain cancer, cervical cancer, gastrointestinal cancer, genitourinary cancer, head and neck cancer, lung cancer, pancreatic cancer, prostate cancer, renal cancer, skin cancer, and testicular cancer.

24. The method of claim 19, wherein the subject is irradiated at a fluence rate of from about 3 $mW/cm^2$ to about 50 $mW/cm^2$.

25. The method of claim 24, wherein the fluence rate is from about 5 $mW/cm^2$ to about 20 $mW/cm^2$.

26. The method of claim 19, wherein the subject is irradiated at a wavelength of from about 500 nm to about 900 nm.

27. The method of claim 19, wherein from about 0.1 to about 48 hours after step (a), the subject is irradiated.

28. The method of claim 19, further comprising administering an anticancer drug to the subject, thereby causing a reduction of at least one of surface area, depth, and amount of tissue affected by the cancerous tissue.

29. The method of claim 28, wherein the anticancer drug is a nanoparticle.

30. The method of claim 28, wherein the anticancer drug is an antibody selected from the group consisting of Cetuximab, Panitumumab, Trastuzumab, Pertuzumab, Ado-trastuzumab emtansine, Bevacizumab, Ipilimumab, Rituximab, Ofatumubab, Alemtuzumab, Brentuximab vedotin, and Gemtuzumab ozogamicin.

31. A method for treating a cancerous tissue within a subject's body, the method comprising:
(a) administering to the subject the pharmaceutical composition of claim 18; and
(b) irradiating the subject at an effective fluence rate and an effective period,
wherein the method causes a therapeutic injury resulting in the reduction of at least one of surface area, the depth, and the amount of the tissue affected by the cancerous condition.

* * * * *

SEQUENCE LISTING

```
<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: Synthetic construct

<400> SEQUENCE: 1

Cys Asp Cys Arg Gly Asp Cys Phe Cys
1               5

<210> SEQ ID NO 2
<211> LENGTH: 64
<212> TYPE: DNA
<213> ORGANISM: Artificial Sequence
<220> FEATURE:
<223> OTHER INFORMATION: Synthetic construct

<400> SEQUENCE: 2
atataccatg ggctgcgact gccgcggaga ctgcttctgc ggaggcggag gcaccaccgc      60
gtct                                                                  64

<210> SEQ ID NO 3
<211> LENGTH: 24
<212> TYPE: DNA
<213> ORGANISM: Artificial Sequence
<220> FEATURE:
<223> OTHER INFORMATION: Synthetic construct

<400> SEQUENCE: 3
ccagactcga gttagctctc atca                                            24
```